US010882266B2

(12) United States Patent
Britton

(10) Patent No.: US 10,882,266 B2
(45) Date of Patent: Jan. 5, 2021

(54) HEATED PRESS UTILIZING A PIVOTING ACTUATING TRUSS FOR EXTRACTION OF OILS

(71) Applicant: Benjamin Ross Britton, Denver, CO (US)

(72) Inventor: Benjamin Ross Britton, Denver, CO (US)

( * ) Notice: Subject to any disclaimer, the term of this patent is extended or adjusted under 35 U.S.C. 154(b) by 176 days.

(21) Appl. No.: 15/904,164

(22) Filed: Feb. 23, 2018

(65) Prior Publication Data

US 2019/0263079 A1  Aug. 29, 2019

(51) Int. Cl.
  *B30B 9/04* (2006.01)
  *A61K 36/185* (2006.01)
  *C11B 1/08* (2006.01)
  *B30B 15/34* (2006.01)

(52) U.S. Cl.
  CPC ............ *B30B 9/047* (2013.01); *A61K 36/185* (2013.01); *B30B 15/34* (2013.01); *C11B 1/08* (2013.01); *A61K 2236/31* (2013.01); *A61K 2236/37* (2013.01)

(58) Field of Classification Search
  CPC ....... B30B 9/047; B30B 15/34; A61K 36/185; A61K 2236/31; A61K 2236/37; C11B 1/08
  See application file for complete search history.

(56) References Cited

U.S. PATENT DOCUMENTS

| | | | | |
|---|---|---|---|---|
| 3,876,361 | A * | 4/1975 | Irwin | B29C 51/32 425/451.6 |
| 10,196,582 | B1 * | 2/2019 | Black | C11B 1/08 |
| 2015/0359256 | A1 * | 12/2015 | Wettlaufer | B30B 9/045 100/37 |
| 2018/0008655 | A1 * | 1/2018 | Weikel | A61K 36/185 |
| 2018/0178473 | A1 * | 6/2018 | Perez | B30B 15/064 |
| 2018/0257326 | A1 * | 9/2018 | Sitnik | B30B 15/065 |
| 2018/0297310 | A1 * | 10/2018 | Evans | A47J 19/06 |
| 2018/0340133 | A1 * | 11/2018 | Carbone | C11B 1/10 |

* cited by examiner

*Primary Examiner* — Anthony J Weier
(74) *Attorney, Agent, or Firm* — Block 45 Legal, LLC

(57) ABSTRACT

A heat press for extracting fluid, such as oil, from a biological plant. A lower heat platen is fixedly attached to a main frame and an upper heat platen is retractably positioned opposite to the lower heat platen. A pneumatic or hydraulic cylinder or a manual or electronic linear actuator provides pressure to an actuation means that is operatively connected to the upper heat platen for initiating movement. A control mechanism that consists of a single pressure regulator system or a dual pressure regulator system is used to control pressure of a pressing operation of the heat press. Alternatively, a digital regulator system can be used to control pressure, time, and temperature of a pressing operation of the heat press. At least one of the upper and lower heat platens has embedded heating elements and an isolated thermocouple. A user interface panel, having an LCD display, a user keyboard, or a touchscreen display is also mounted to the main enclosure.

22 Claims, 22 Drawing Sheets

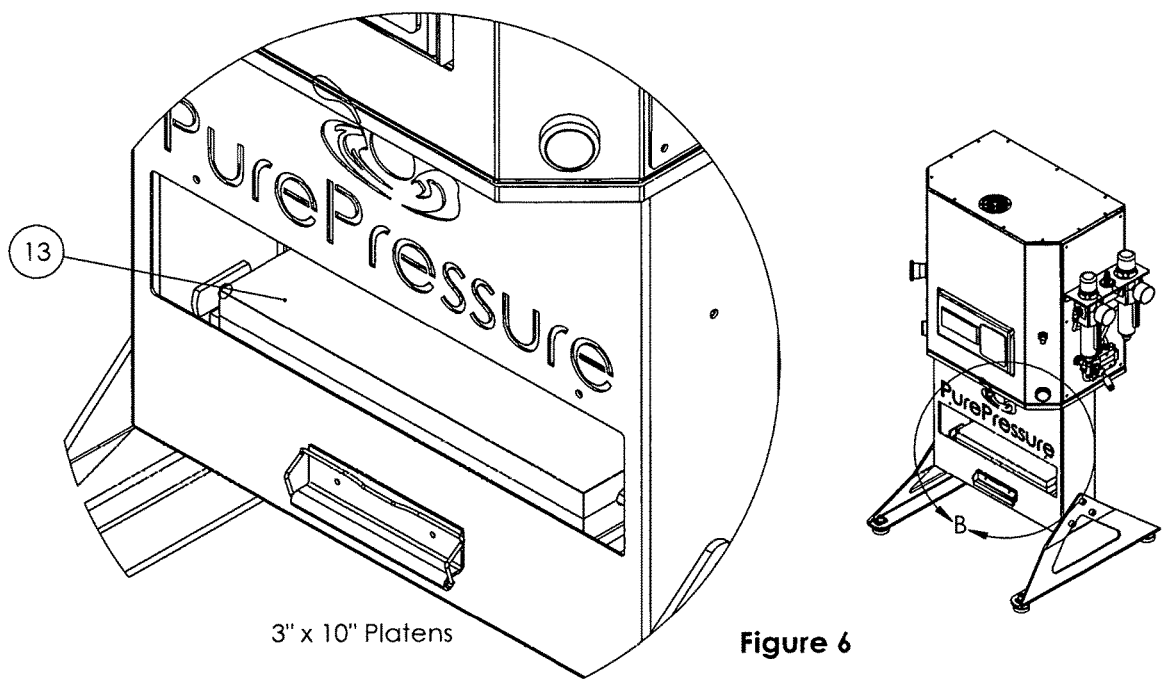
3" x 10" Platens    Figure 6
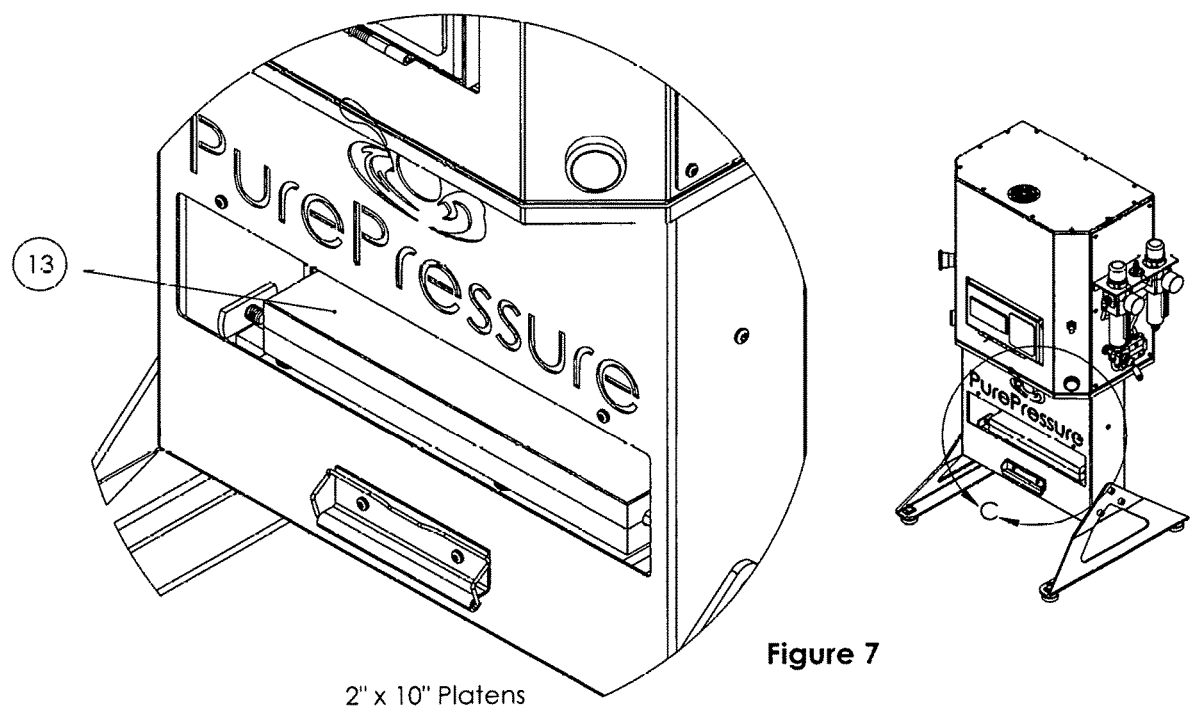
2" x 10" Platens    Figure 7

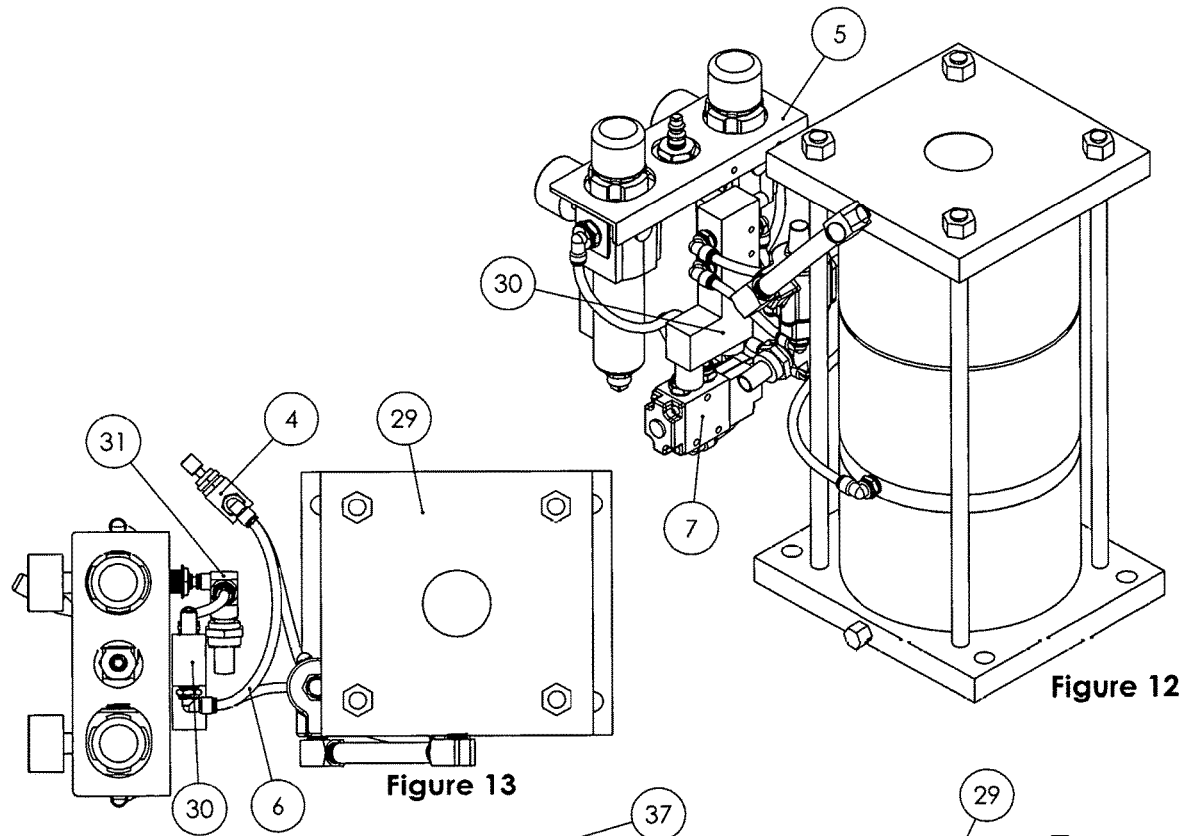
Figure 12
Figure 13
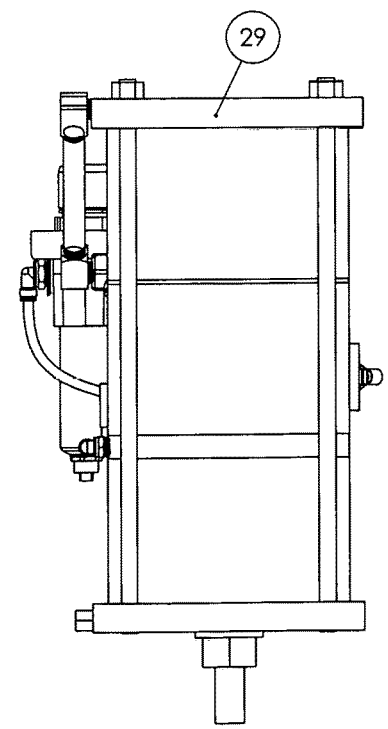
Figure 14
Figure 15

SECTION M-M

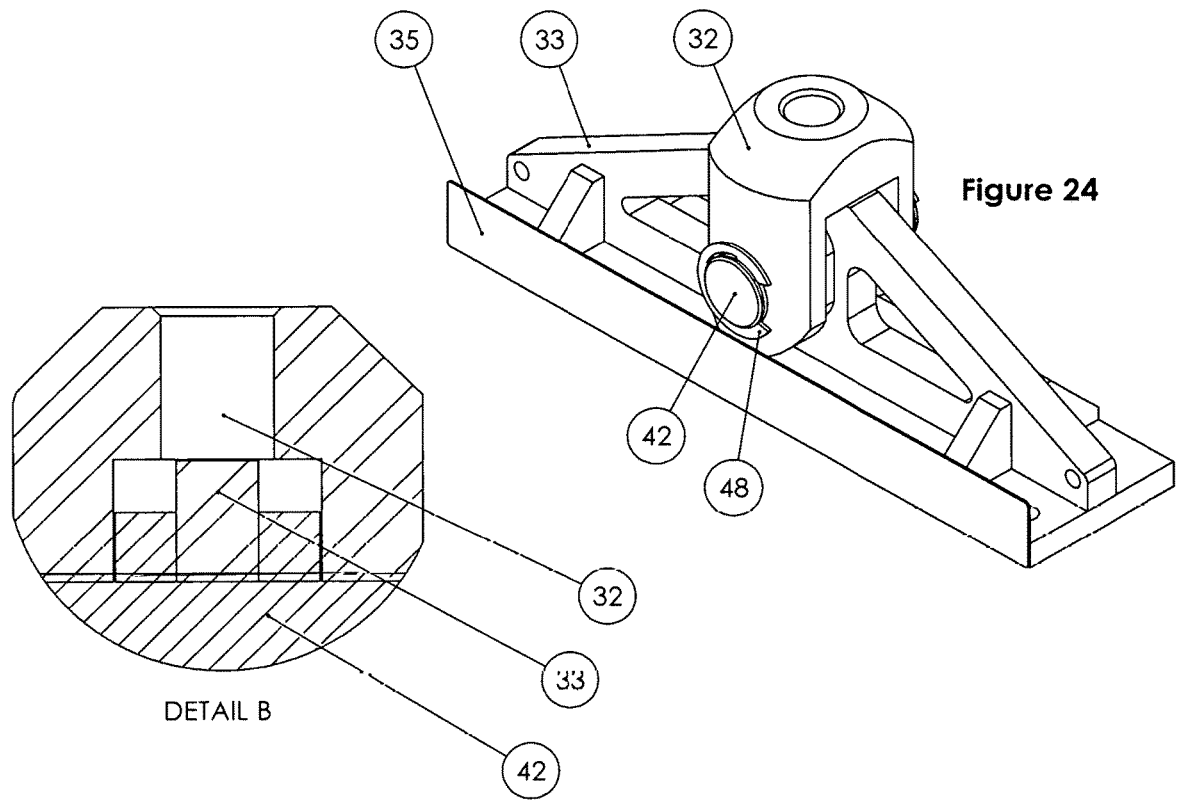
Figure 24
DETAIL B
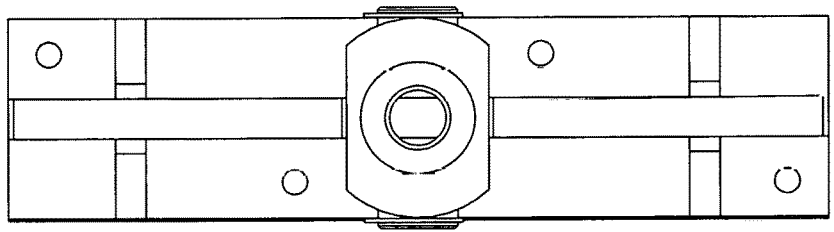
Figure 25
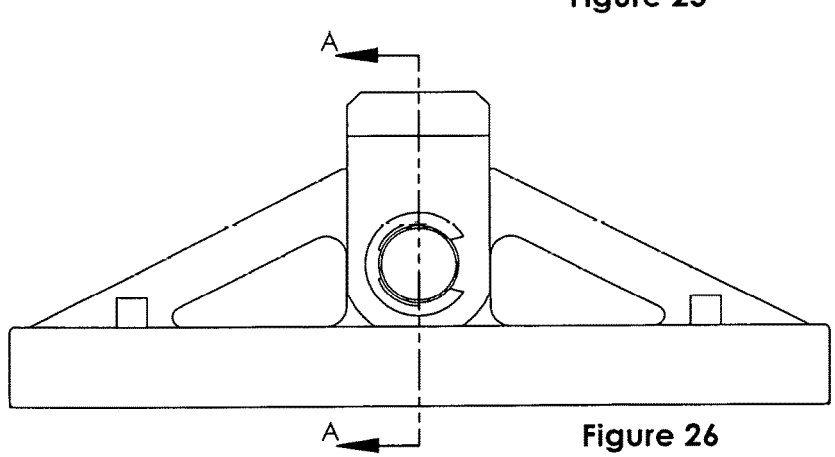
Figure 26
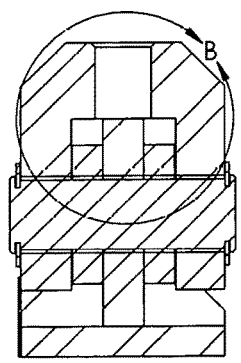
SECTION A-A
SCALE 1 : 2

HEATED PRESS UTILIZING A PIVOTING ACTUATING TRUSS FOR EXTRACTION OF OILS

RELATED PATENT APPLICATION

The present application is related to provisional patent application no. 62/463,633, for HEATED PRESS UTILIZING A PIVOTING ACTUATING TRUSS filed Feb. 25, 2017, and hereby incorporates the teaching therein by reference.

FIELD OF THE INVENTION

This invention relates to heated presses and, more particularly, to a heated press utilizing a pivoting actuating truss for extraction of oils.

BACKGROUND OF THE INVENTION

Cannabis extract has wide-ranging beneficial effects on a number of medical conditions. Chronic pain has been shown to be controlled by use of cannabis. Use of a topical application of cannabis extract in dermal penetrating cream has been effective in relieving chronic pain conditions of arthritis and tendonitis. The use of a topical application of the extract in a penetrating cream formulation allows the medication to directly affect the local receptor sites. This direct application at the affected sites allows rapid modulation of the pain and inflammation of these chronic conditions.

A specific pain condition that has been effectively treated by the use of cannabis extract is fibromyalgia. This chronic debilitating condition involves local pain at specific sites on the body. The use of this extract allows stimulation of the CB2 receptor sites in the local pain areas as well as stimulation of the CB1pns receptors. This disease, which is a combination of autoimmune and inflammatory conditions, responds extremely well to topical applications of cannabis extract.

Autoimmune diseases also seem to respond very well to the application of cannabis extract. This is because of the action on the CB2 receptors which are located on several different cells lines in the immune system. Through the inhibition of TCF-alpha cannabis has a beneficial effect on patients with multiple sclerosis and lupus. These severe and chronic autoimmune diseases have been shown in several studies to respond to smoked cannabis. Topical application is effective without the psychoactive side effects. By selective stimulation of the CB2 receptors the immune modulation effects of the cannabis extract have a beneficial effect on multiple sclerosis and lupus without the central nervous system effects.

Nausea and vomiting that are unresponsive to other medications have been shown to be helped through the use of cannabis. The use of cannabis extract has a modulating effect on nausea and vomiting without the psychoactive properties that smoking the Cannabis plant can cause in a mammal. This has been shown to be especially useful in helping with the side effects of chemotherapy. Additionally animal studies show an increase in hunger and feeding behavior through the action of the CB2 receptors.

Applying topical cannabis extract has a positive effect on the healing of psoriasis lesions. The cannabis plant contains resinous trichrome structures which are the source of cannabinoids, such as tetrahydrocannabinol (THC) and cannabidiol (CBD). Devices and methods of using cannabis ideally seek to separate the trichromes from the accompanying plant material. However, the plant material contains terpenoids and flavonoids, which provide desirable odor and flavor as well as a beneficial synergistic entourage effect. The traditional method of using cannabis has been to smoke the leaves and buds of the plant, but the combustion of the whole plant material introduces noxious components to the body in addition to desirable cannabinoids, terpenoids, and flavonoids.

To maximize the production and preservation of the cannabinoid, terpenoid, and flavonoid components, while minimizing the amount of plant material, a number of extraction methods have been used. Rosin refers to a resinous extract product created from an extraction process applied to cannabis starting material that utilizes a combination of heat and pressure. With cannabis, the heat and pressure method can be used either with flowers or less desirable leaves of the cannabis plant and can also be used to clean up water hash and sifted kief into a full-melt hash oil of high purity. The result is a translucent, sappy, and sometimes clear and brittle glass-like product. If executed correctly, rosin can rival or surpass the flavor, potency, quality, and yield of other solvent-based extraction products with increased safety and ease. One reason for rosin's popularity is that it is a solvent-less technique, so the process does not require the use of volatile hydrocarbon solvents. Instead, rosin uses a mechanical process involving heat and pressure to extract the desired components from the plant.

Solvent extraction systems utilize light hydrocarbons such as butane and/or propane as solvents. Often, these complex and mechanical systems require a lengthy purge to safely remove most of the residual solvents from the final product. Rosin, however, simply uses heat and pressure and does not require additional processing, so the final product is clean and ready in minutes. When compared to butane hash oil (BHO), the two can be aesthetically indistinguishable. Rosin, when made properly, retains as many or more valuable terpenoids and flavonoids that provide aroma and flavor, as well as clinically proven synergistic entourage effects. However, rosin does not contain residual hydrocarbons, giving it an "organic" quality.

Devices and methods for making rosin have included using a hair straightening iron to produce the necessary heat and pressure for producing the rosin extract. In this method the cannabis starting material is usually contained between two pieces of parchment paper and the extracted rosin seeps onto the paper, then scraped from the paper with a collection tool.

DESCRIPTION OF RELATED ART

U.S. Pat. No. 3,998,580 issued to Pffiffer for PRESS SPAR FOR HEATED PANEL PRESS on Dec. 21, 1976 describes a press spar construction for heated panel presses producing composite chipboard panels and the like, in which the pressure plates, in order to avoid heat distortion, are insulated from the press spars by means of pressure-resistant, water-repellant insulating blocks of high dimensional stability, which insulating blocks are encased in metallic shrouds so as to avoid friction on the insulating material.

U.S. Pat. No. 4,963,221 issued to Isobe, et al. for HOT PRESS INCLUDING CAM ROD PENETRATING TOP PLATEN on Oct. 6, 1990 describes a hot press to manufacture a substrate in which a printed circuit is provided. The hot press comprises at least one vertically movable heating plate, a freely elevating movable platen which elevates the heating plates to press a plate to be treated between the heating plates, and a detecting means for detecting the movement of the uppermost heating plate when said uppermost heating plate starts to be elevated, in which the elevating speed of the movable platen is changed to a lower speed by a signal generated from the detecting device.

U.S. Pat. No. 5,379,689 issued to Timmons, et al. for COMPOSITE REPAIR PRESS FOR MANUFACTURING AND REPAIRING A WORKPIECE MADE FROM A COMPOSITE MATERIAL on Jan. 10, 1995 describes a multipurpose, automatic, self-contained device for manufacturing or repairing a workpiece made from a composite material. The device includes a frame having an upper frame member and a lower frame member. A mechanical apparatus for providing a compressive force is mounted to the lower frame member and a lower platen is mounted to a movable member of the apparatus. At least one heater is associated with at least one of the platens to apply heat to the workpiece and at least one temperature sensor is provided for mounting to the workpiece. The lower platen is moved toward and away from the upper platen by the mechanical apparatus to apply a compressive force to the workpiece disposed between the platens as a function of the temperature sensed from the workpiece and/or according to a predetermined schedule or plan.

U.S. Pat. No. 6,026,738 issued to Charles, et al. for SELF-CONTAINED CRUST FACTORY on Feb. 22, 2000 describes a self-contained pizza crust factory for creating a docked, formed pizza crust from a raw dough ball and positioning the crust on a crust container. The pizza crust factory includes an infeed conveyor belt that transports the ball of raw dough from an infeed end of the apparatus to a press assembly. The press assembly includes an upper platen and a lower platen positioned on opposite sides of the infeed conveyor belt. The upper platen of the press assembly is heated and in close contact with a crust die plate that is removably secured within a die holder assembly.

U.S. Pat. No. 6,655,268 issued to Comley, et al. for COMPACT HOT PRESS on Dec. 2, 2003 describes a portable, compact hot press that includes a frame that has a press unit attached thereto. The press unit has a crown plate, a bolster plate, and a base plate. An upper press unit is attached to the crown plate and a lower press unit is attached to the bolster plate. The lower press unit is configured to contact the upper press unit when the press is in a closed position. The press further includes a control unit attached to the frame, configured to manually or automatically control press operation. Additionally, the press includes a hydraulic unit that is attached to the frame and is configured to facilitate motion of the press operation.

U.S. Pat. No. 8,689,685 issued to Lawrence for DOUGH FORMING PRESSING PLATE WITH SPACERS on Apr. 8, 2014 describes a dough pressing system that includes a cover coupled to a pressing platen, wherein the cover can reduce the wear caused to the pressing platen by the heat and pressure used to process one or more products.

U.S. Published Patent Application 2018/0008655 on application by Weikel for PRESS DEVICE AND METHOD FOR PRODUCING RESINOUS PLANT EXTRACT published on Jan. 18, 2018, describes a rosin press adapted for operation in two dimensions or orientations so that collection efficiency and amount of rosin from the device is maximized. The press applies pressure to a quantity of resinous plant material placed between a pair of heated platens to initiate a flow of rosin. The press can be rotated from a first dimension to a second dimension so that the flow of rosin can fall by gravity to a chilled surface and be more easily collected while preserving quality.

SUMMARY OF THE INVENTION

In accordance with the present invention, there is provided a heat press for extracting fluid from a biological plant. A lower heat platen is fixedly attached to a main frame and an upper heat platen is retractably positioned opposite to the lower heat platen. A pneumatic or hydraulic cylinder or a manual or electronic linear actuator provides pressure to an actuation means that is operatively connected to the upper heat platen for initiating movement. It should be understood that in the preferred embodiment, the upper heat platen is moveable and the lower heat platen is stationary, but in other embodiments, either heat platen may be stationary or moveable with respect to one another. Control means that consists of a single, a dual, or a digital pressure regulator system is used to control pressure of a pressing operation of the heat press. At least one of the upper and lower heat platens has embedded heating rods and an isolated thermocouple. A user interface panel, having an LCD display and a user keyboard or a touchscreen display, is also mounted to the main enclosure.

It is therefore an object of the invention to provide a heat press for extracting oils and other fluids from biological plants.

It is another object of the invention to provide such a heat press that uses single, dual, or digital pressure regulator system.

It is a further object of the invention to provide a heat press having an actuation speed controller.

It is still another object of the invention to provide a heat press with swappable, different heat platen sizes.

It is yet another object of the invention to provide a heat press capable of operating in horizontal and vertical orientations.

It is another object of the invention to provide a heat press with modular and replaceable press components, including a modular and removable electrical enclosure.

It is yet another object of the invention to provide a mechanism to actuate and distribute pressure that includes a predetermined truss/clevis gap.

It is yet another object of the invention to provide a supply of parchment paper and parchment paper retaining clips.

These and other objects and advantages of the present invention are more readily apparent with reference to the following detailed description and the accompanying drawings.

BRIEF DESCRIPTION OF THE DRAWINGS

A complete understanding of the present invention may be obtained by reference to the accompanying drawings, when considered in conjunction with the subsequent detailed description, in which:

FIG. 6 is a front schematic view of a heated press with insert showing 3"×10" platens;

FIG. 7 is a front schematic view of a heated press with insert showing 2"×10" platens;

FIG. 12 is a perspective view of a dual pressure regulator system with pressure control lever;

FIG. 13 is a plan view of a pneumatic cylinder, pneumatic tube, and pressure transducer;

FIG. 14 is a front schematic view of a pneumatic cylinder with cylinder inlets and cylinder rod;

FIG. 15 is a right schematic view of the pneumatic cylinder with cylinder inlets and cylinder rod shown in FIG. 14;

FIG. 24 is a perspective view of a clevis and actuating truss;

FIG. 25 is a plan view of clevis and actuating truss shown in FIG. 24;

FIG. 26 is a front view of clevis and actuating truss shown in FIG. 24;

Like reference numerals refer to like parts throughout the several views of the drawings.

DETAILED DESCRIPTION OF THE PREFERRED EMBODIMENT

Although the following detailed description contains specific details for the purposes of illustration, those of ordinary skill in the art will appreciate that variations and alterations to the following details are within the scope of the invention. Accordingly, the exemplary embodiments of the invention described below are set forth without any loss of generality to, and without imposing limitations upon, the claimed invention.

The invention is a heat press for extracting fluid from a biological plant. A lower heat platen is fixedly attached to a main frame and an upper heat platen is retractably positioned opposite to the lower heat platen. A pneumatic or hydraulic cylinder or a manual or electronic linear actuator provides pressure to an actuation means that is operatively connected to the upper heat platen for initiating movement. Although in the preferred embodiment the upper heat platen is moveable and the lower heat platen is stationary, in other embodiments, either heat platen may be stationary or moveable with respect to one another. Control means that consists of a single pressure regulator system, a dual pressure regulator system, or a digital pressure regulator system is used to control pressure of a pressing operation of the heat press. The modular nature of the inventive apparatus allows for individual components to be upgraded, replaced, or repaired in the field.

Figure 1:
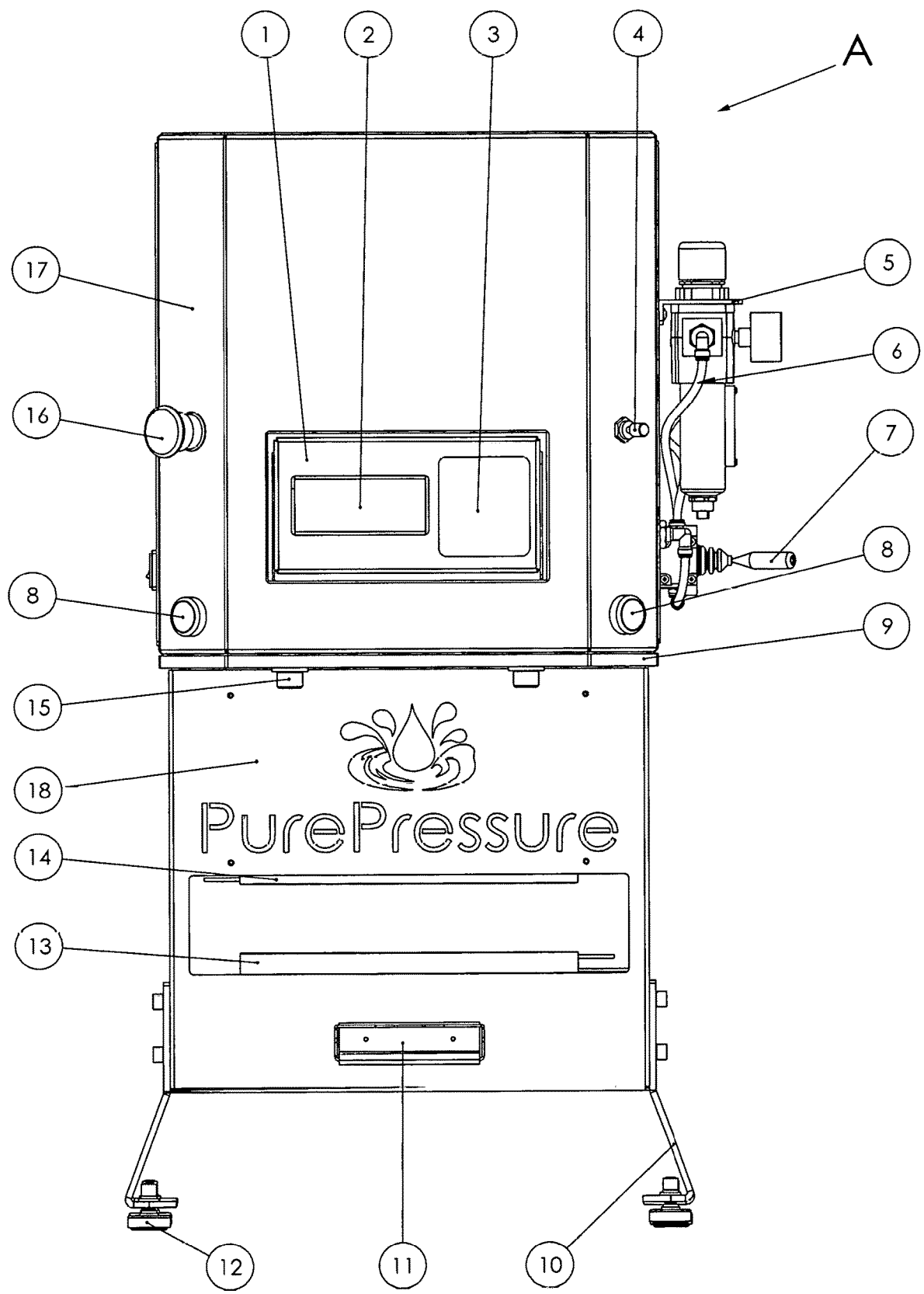
FIG. 1 is a front schematic view of a heated press in accordance with the present invention.

Referring now to FIG. 1, there is shown a front schematic view of a heated press identified by reference letter "A" in accordance with the present invention. A main frame 9, preferably made of steel or other strong metal or alloy, forms the structure on or in which all components are mounted. At the upper portion of main frame 9 is a main enclosure 17 that contains pneumatic and electrical components, discussed in greater detail hereinbelow.

On the lower portion of main frame 9 is mounted a lower heat platen 13 and an upper heat platen 14, enclosed by a platen cover 18. Parchment paper and parchment paper retaining clips 11 are stored in and extracted from the lower portion of main frame 9, as needed. Main frame 9 is supported by vertical orientation legs 10 that terminate in standard, threaded leveling feet 12 to provide stability on uneven surfaces. In alternate embodiments, leveling feet 12 could be replaced with bearings and cotter pins, a hinged base, a counterweight system, pulleys and cables, or any other mechanically rotating system known to those of skill in the art.

Main enclosure 17 is secured to the heat platen cover 18 at the lower portion of main frame 9 by means of conventional cylinder mount hardware 15.

The upper portion of main frame 9 supports main enclosure 17, as described, as well as a dual pressure regulator system 5, in one embodiment, comprising a 3-position pressure control lever 7, an actuation start button 8, an emergency stop button 16, a manually operated actuation speed controller 4, and a pneumatic tube 6, which directs compressed air through pneumatic panel 19 into main enclosure 17. In alternate embodiments, pressure control lever 7 could be replaced with another valve, such as an electronic solenoid valve or a digital pressure regulator, not shown.

Actuation speed controller 4 controls the speed of movement of upper heat platen 14, relative to fixed lower heat platen 13 (FIG. 16) by throttling exhaust air on the opposite side of the pneumatic piston. In alternate embodiments, actuation speed controller 4 can control upper heat platen 14 movement by throttling or restricting airflow in other locations in the pneumatic system. Moreover, manually controlled actuation speed controller 4 can be replaced with an electronically or even an automatically controlled system in alternate embodiments.

Mounted to the front face of main enclosure 17 are electronic components and indicators, including a hinged user interface panel 1, an LCD display 2, and a user keypad 3. In alternate embodiments, user interface panel 1 can be fixed or mounted remotely or contained on a separate electronic device, such as a computer, tablet, integrated touchscreen, or smart phone, and actuation may be controlled directly through the user interface or through external buttons and switches, not shown.

Figure 2:
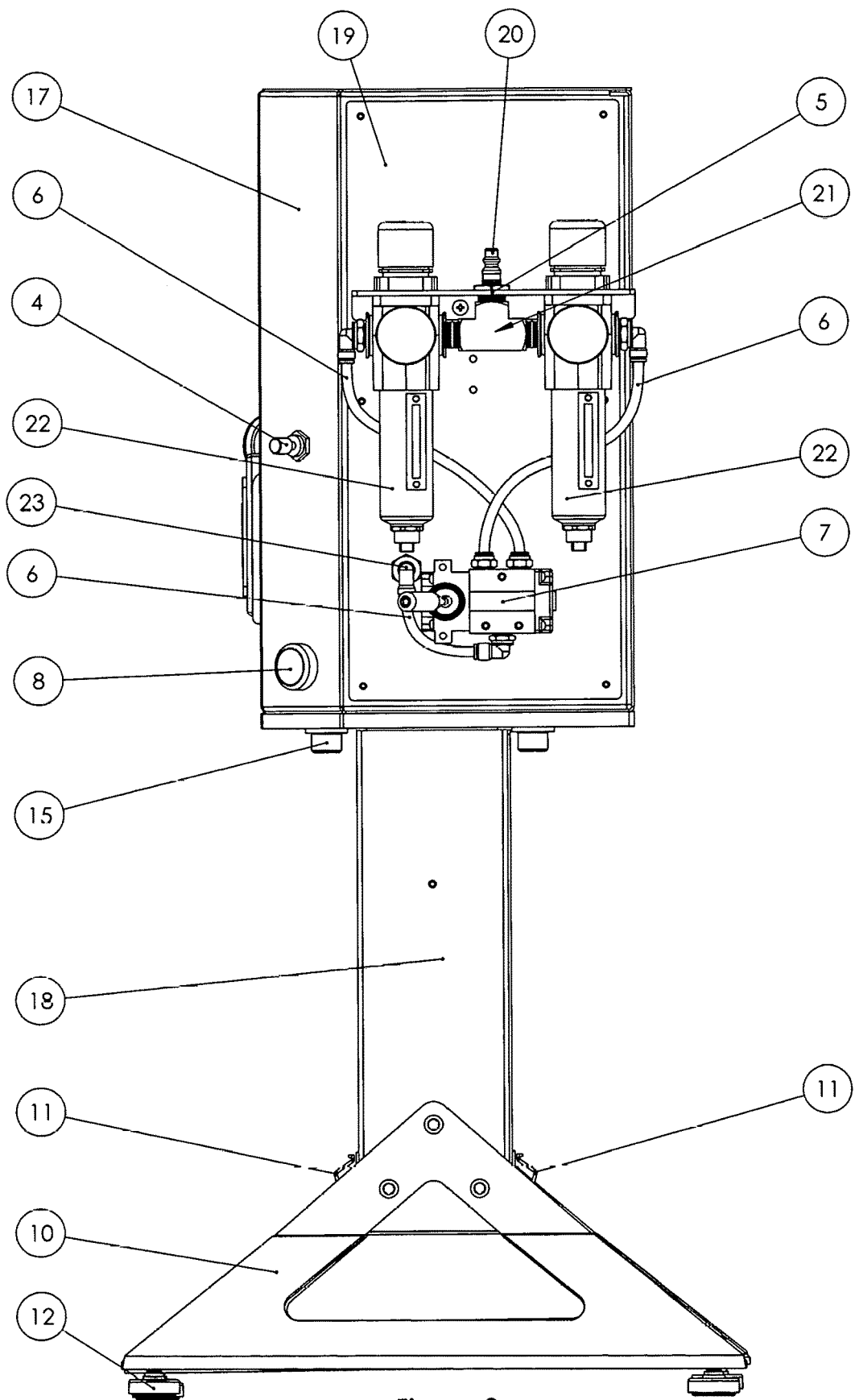
FIG. 2 is a side schematic view of a pneumatic panel of the heated press shown in FIG. 1.

Referring now also to FIG. 2, there is shown a side schematic view of a removable pneumatic panel 19 attached to main frame 9 of heated press A. On pneumatic panel 19 are mounted pneumatic components: a pneumatic bulkhead 23, a dual pressure regulator system 5 having two manual/automatic pressure regulators 22, corresponding pneumatic tubes 6, an inlet air quick connect device 20, and a female pipe tee 21, which divides compressed air to both manual/automatic pressure regulators 22. The pressure regulator 22 consists of one or more auto draining, air filtering, moisture separating regulators, or any other type of compressed air regulators for regulating compressed air pressures supplied to pneumatic cylinder 29.

One of the pressure regulators 22 is set to a lower pressure while the other pressure regulator 22 is set to a higher pressure. These regulated air sources are sent to the pressure control lever 7 via pneumatic tubing 6. Pressure regulator 22 may be mounted externally or internally, removably, or permanently fixed to main enclosure 17. The components of the pneumatic system of heat press A are connected to one another with polyethylene or any suitable composite, forming pneumatic tubing 6 for routing compressed air through all pneumatic components to pneumatic cylinder 29. Dual pressure regulator system 5 is used to manually increase pressure from 0 psi to 140 psi during system operation.

Front and rear parchment paper retaining clips 11 may be used with any heat resistant film or paper including silicone or Teflon or used without a film or paper for alignment of a custom filtration bag. The parchment paper itself, not shown, can be provided in cut sheets. In the preferred emblements, parchment paper clips 11 are made of metal, but in other embodiments, they could be made of plastic. In other embodiments, parchment paper clips 11 could be replaced with magnets, not shown. Their placement is critical in the alignment of the biological plant material to be pressed.

Figure 3:
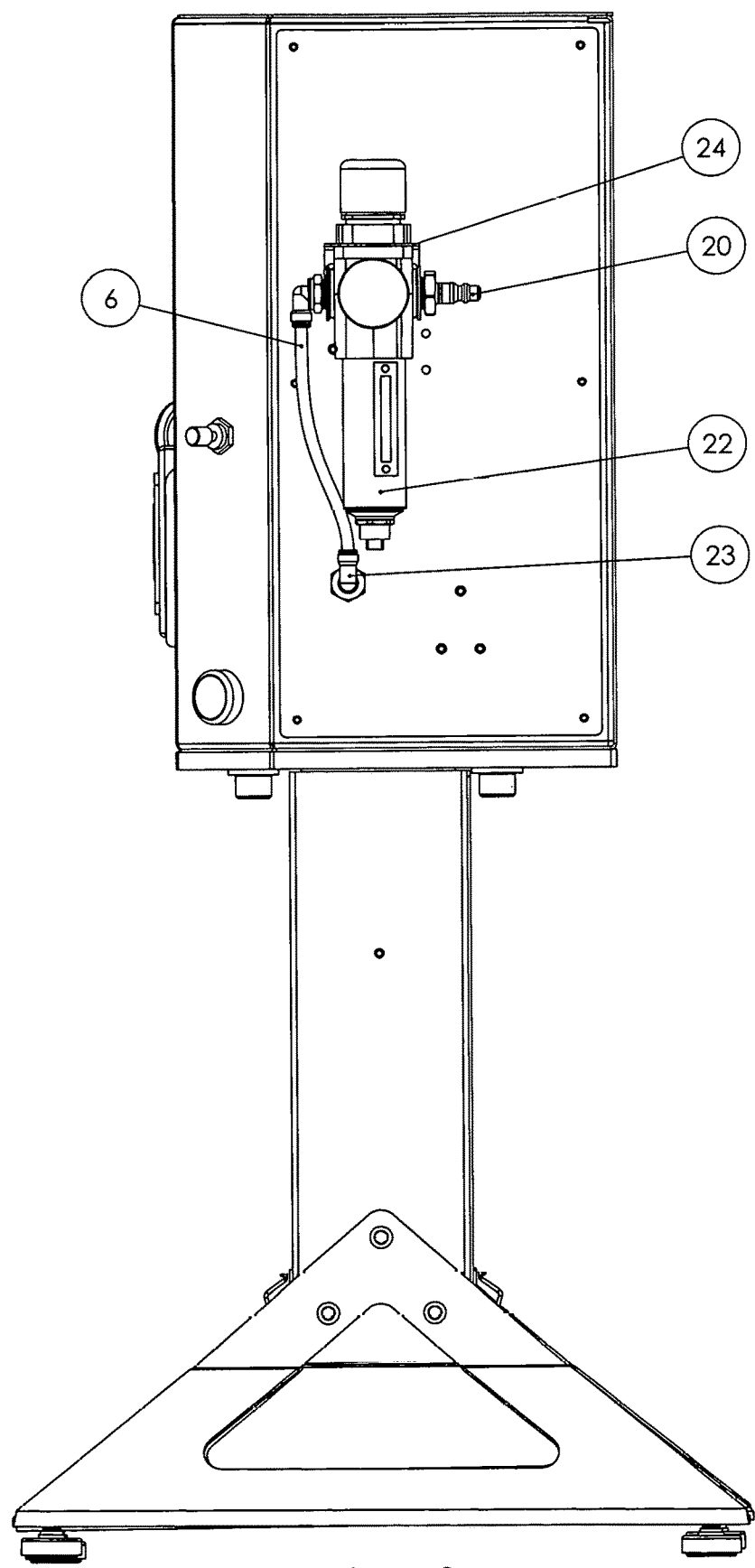
FIG. 3 is a schematic view of a single pressure regulator system and manual/automatic pressure regulator.

Referring now to FIG. 3, there is shown a schematic view of an alternate embodiment of the invention: a single pressure regulator system 24 with a pneumatic bulkhead 23, manual/automatic pressure regulator 22, corresponding pneumatic tube 6, and an inlet air quick connect device 20.

Figure 4:
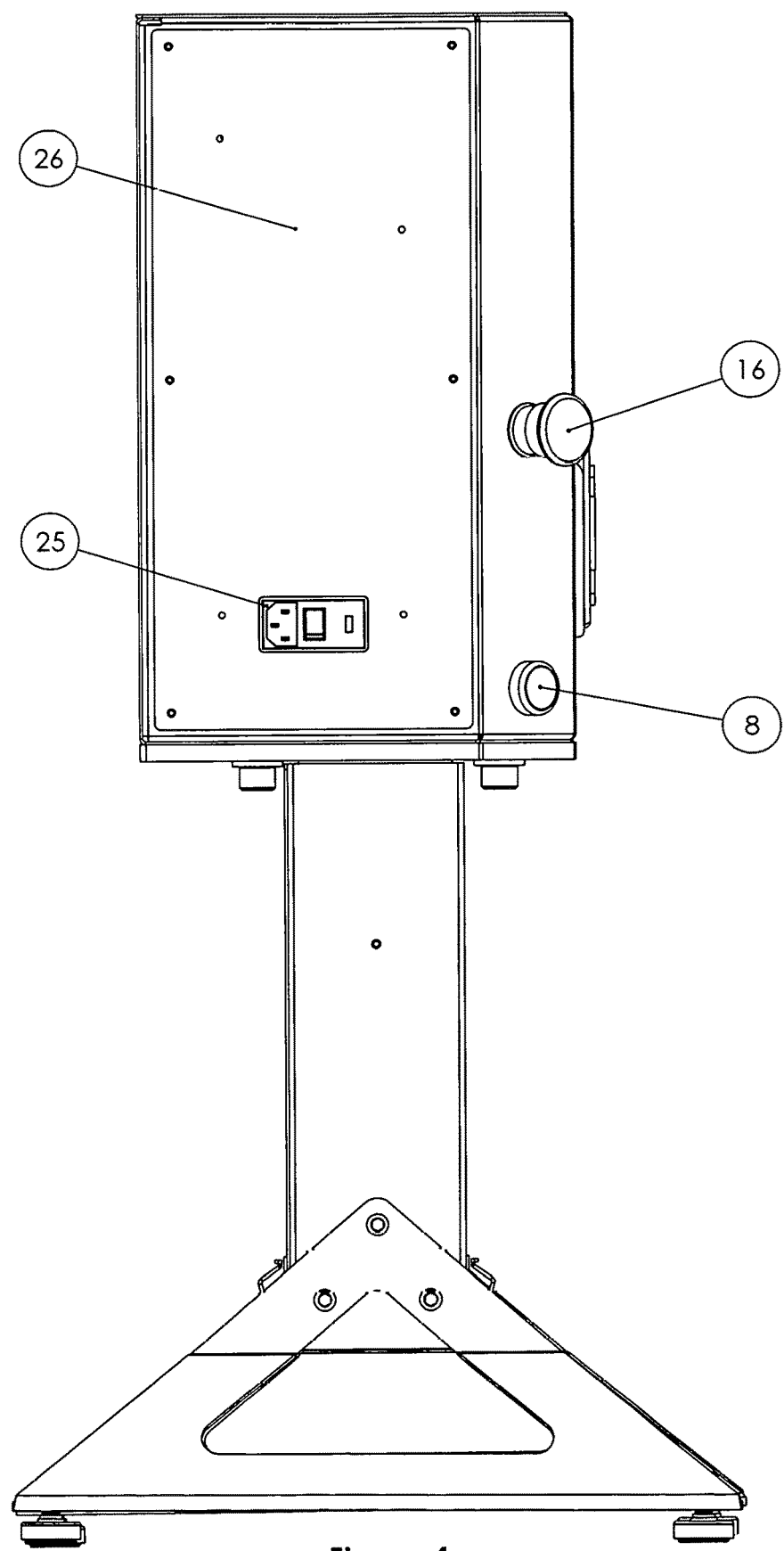
FIG. 4 is a left schematic view of an electrical enclosure and emergency stop button.

Referring now to FIG. 4, there is shown a left schematic view of an electrical enclosure 26 mounted on main frame 9, emergency stop button 16, actuation start button 8, and a power entry module 25, to which is supplied a standard 110 VAC or 240V single phase power electrical power supply, not shown. Electrical enclosure 26 can be removed from main enclosure 17.

Figure 5:
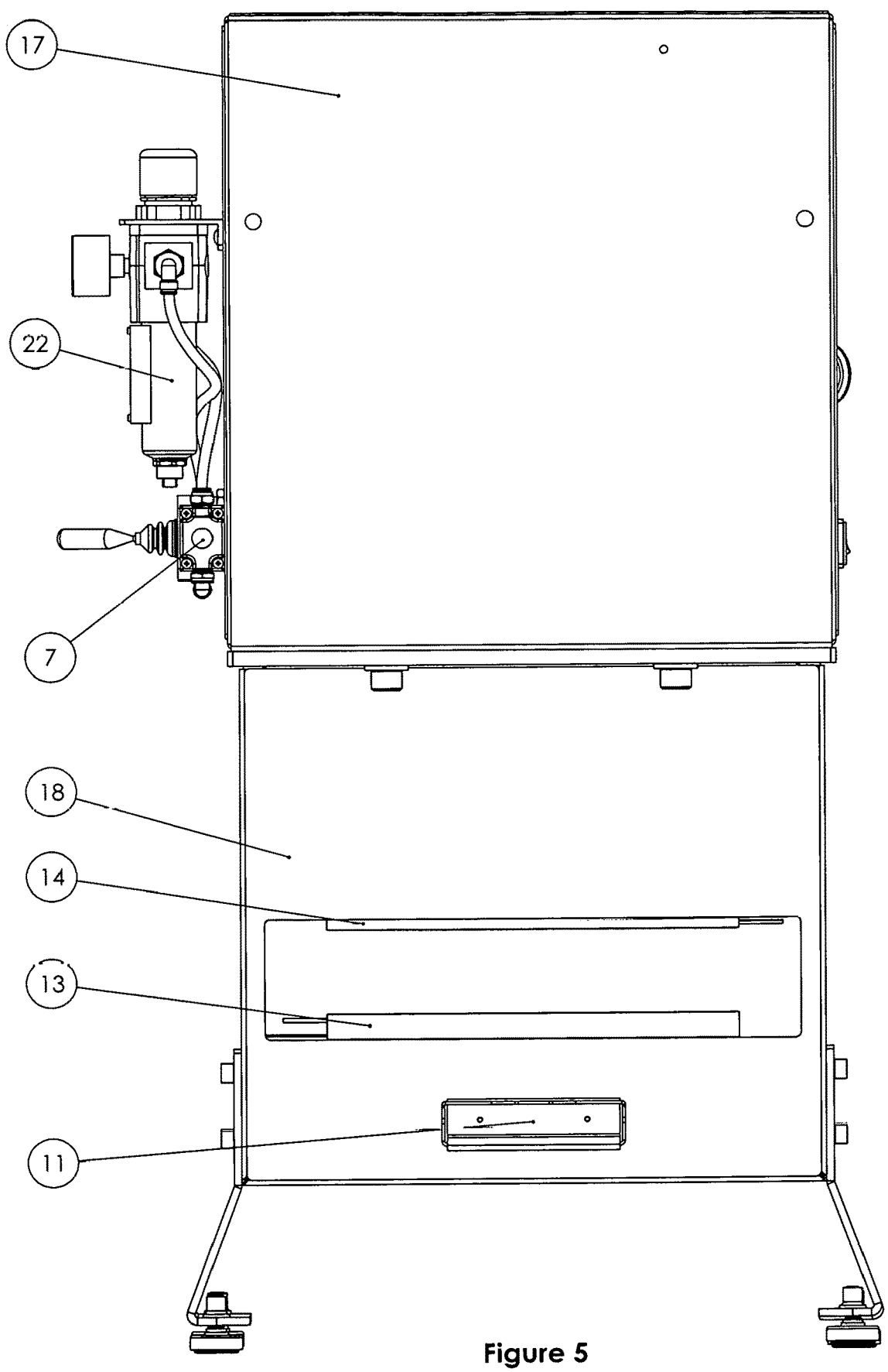
FIG. 5 is a rear schematic view of a main enclosure with pressure regulator system.

Referring now to FIG. 5, there is shown a rear schematic view of main enclosure 17 with single pressure regulator system 24 and pressure control lever 7. As mentioned hereinabove, parchment paper retaining clips 11 hold parchment paper, not shown, in position prior to pneumatic operation of heated press A.

Referring now to FIG. 6, there is shown a front schematic view of a heated press A with insert showing a 3"×10" lower heat platen 13, which is mounted directly to main frame 9 in a fixed position. Both lower and upper heat platens 13, 14 are made from 6061 aluminum and preferably rectangular to provide optimal extraction of essential oils, but the shape of platens 13, 14 can be modified if desired.

Similarly, referring now to FIG. 7, there is shown a front schematic view of a heated press A with insert showing 2"×10" lower heat platen 13. It should be understood that any reasonable size platen dimensions can be used, depending upon the size and capacities of other system components and use requirements. Different sized heat platens 13, 14 can be substituted for the embodiments disclosed.

Figure 8:
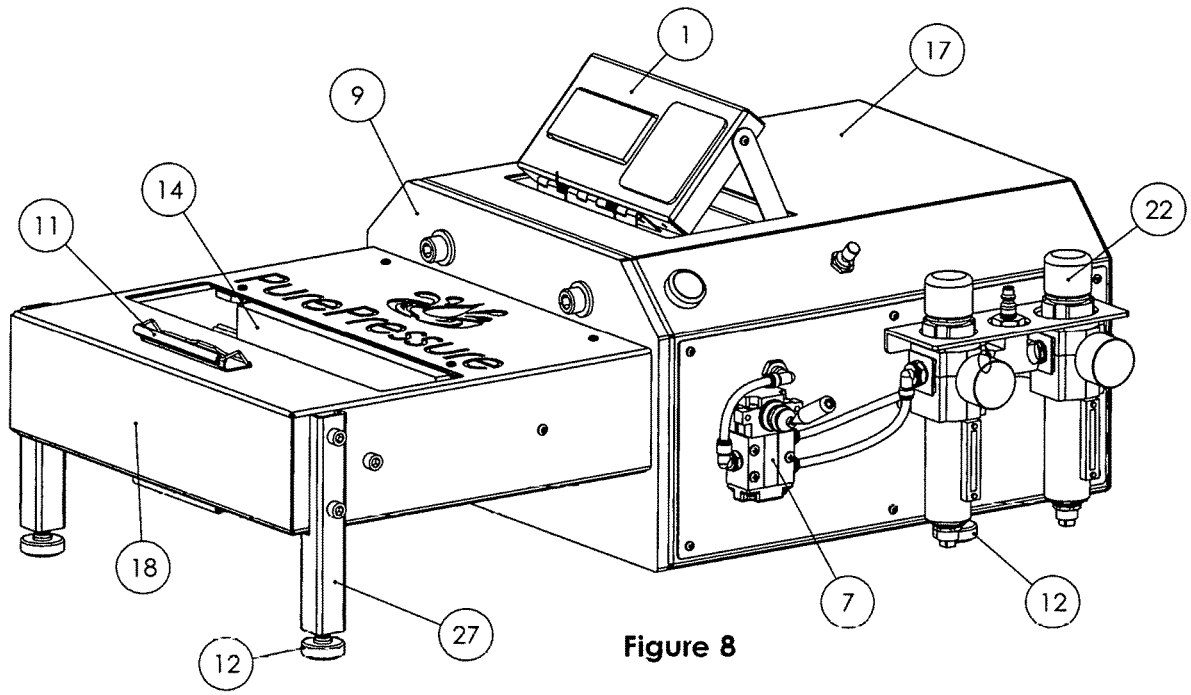
FIG. 8 is a front perspective view of a heated press in a horizontal orientation.

Referring now to FIG. 8, there is shown a front perspective view of a heated press A in a horizontal orientation. In this orientation, upper heat platen 14 is visible, as is pressure controller lever 7. User interface panel 1 is raised at an angle off the major plane of main enclosure 17. Horizontal orientation legs 27 are added to support heat platen assembly 18. Dual pressure regulator system 5 has two manual/automatic pressure regulators 22 connected to pressure controller lever 7.

Figure 9:
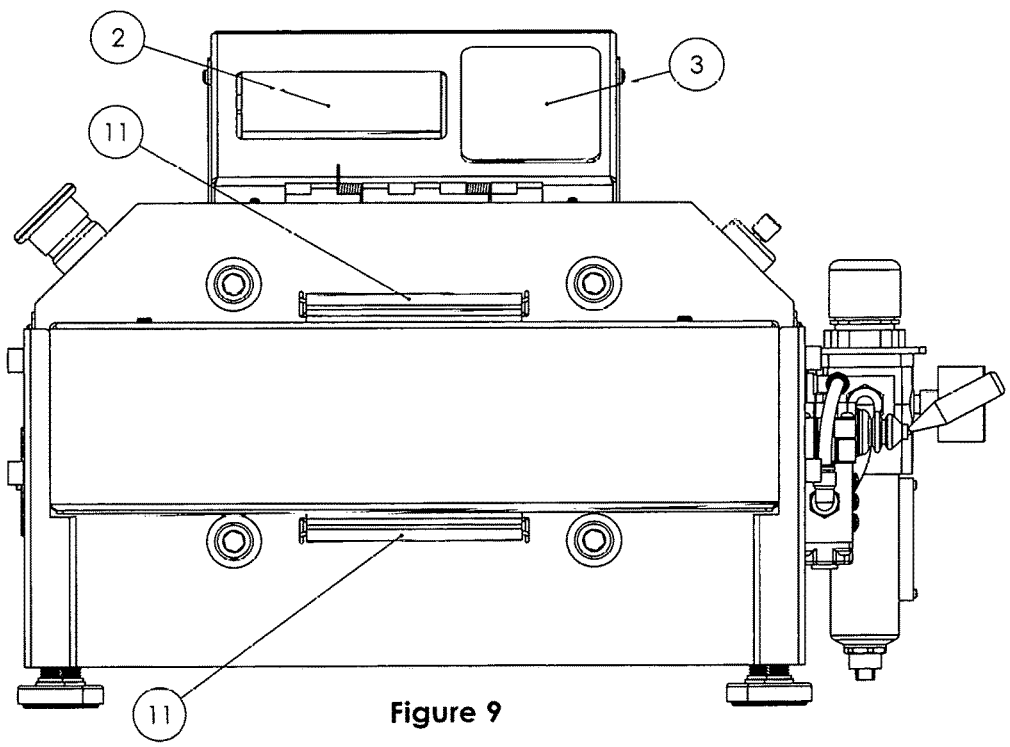
FIG. 9 is a front schematic view of the heated press shown in FIG. 8.

Referring now to FIG. 9, there is shown 9 a front schematic view of the heated press as shown in FIG. 8.

Figure 10:
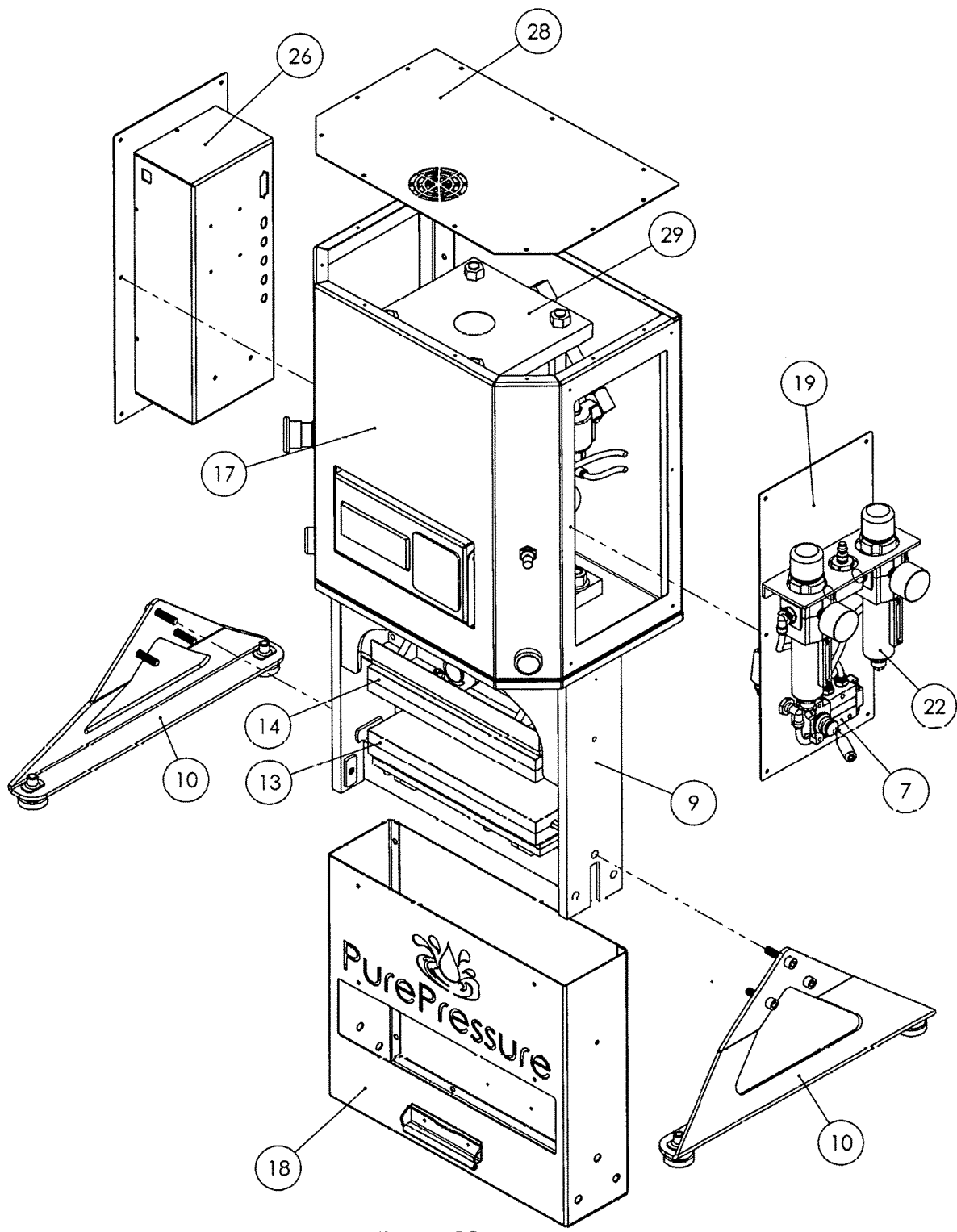
FIG. 10 is an exploded schematic view of a heated press, showing major components thereof.

Referring now to FIG. 10, there is shown an exploded schematic view of a heated press A, showing major components thereof. A slidable platen cover 18 covers main frame 9 and lower and upper heat platens 13, 14. A pneumatic cylinder 29 is disposed within main enclosure 17 which, in turn, is secured to main frame 9. A top vent panel 28 is positioned above and secured to main enclosure 17. Electrical enclosure 26 and pneumatic panel 19 are attached to either side of main enclosure 17, as shown.

Figure 11:
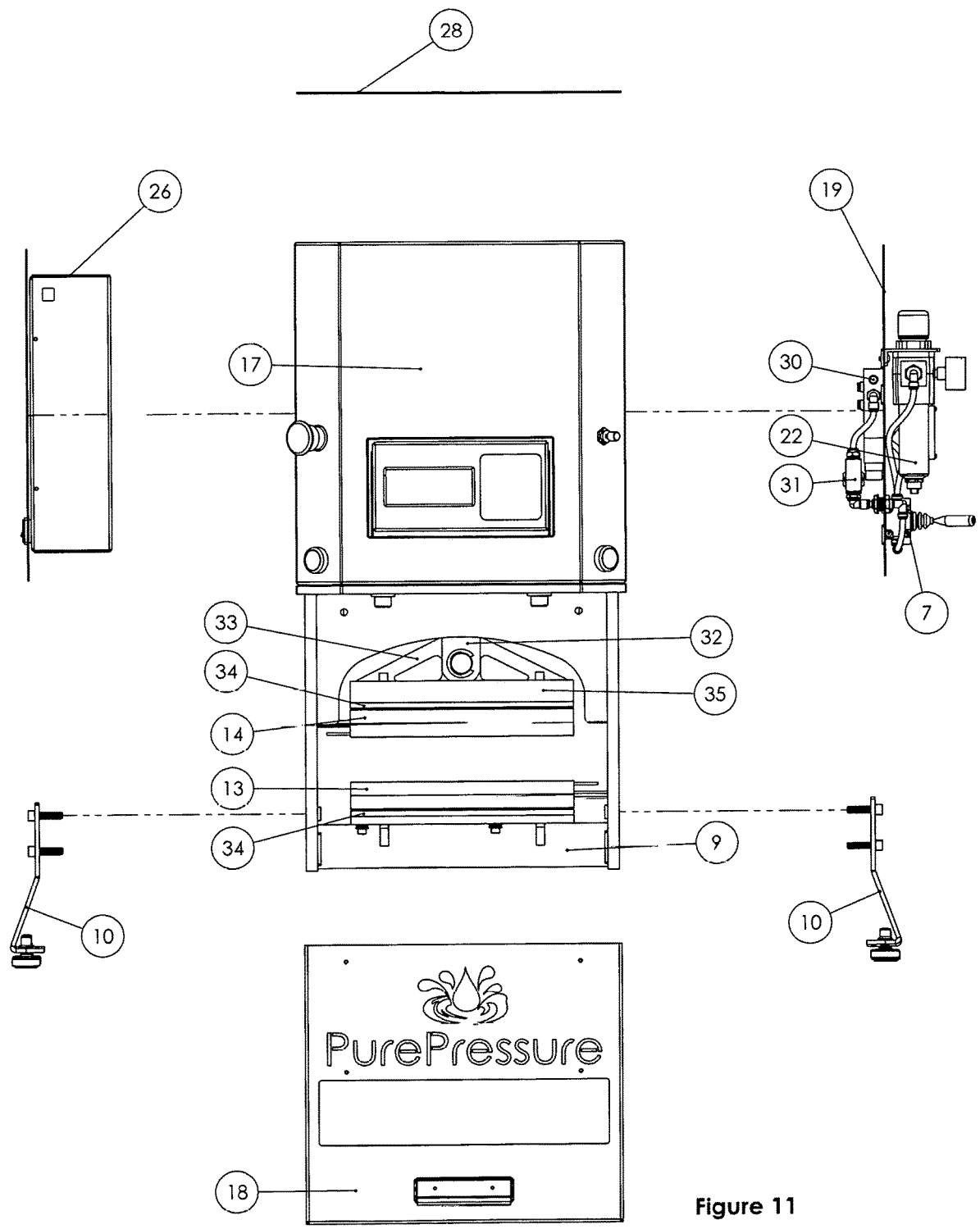
FIG. 11 is an exploded schematic front view of the heated press shown in FIG. 10.

Referring now to FIG. 11, there is shown an exploded schematic front view of the heated press A shown in FIG. 10. Vertical orientation legs 10 are attached to lower main frame 9.

Referring now to FIG. 12, there is shown a perspective view of dual pressure regulator system 5 attached to pneumatic cylinder 29 and pressure control lever 7.

Referring now to FIG. 13, there is shown a plan view of pneumatic cylinder 29, pneumatic tubes 6, actuation speed controller 4, a pressure transducer 31, and a directional solenoid valve 30.

Referring now to FIG. 14, there is shown a front schematic view of pneumatic cylinder 29, manual/automatic pressure regulator 22, pressure control lever 7, quick exhaust valve 36, with a cylinder inlet 37 to extend connected thereto, a cylinder inlet 38 to retract, and a non-rotating cylinder rod 39.

Referring now to FIG. 15, there is shown a right schematic view of pneumatic cylinder 29 with cylinder inlets 37, 38, manual/automatic pressure regulator 22, and cylinder rod 39, as shown in FIG. 14.

Figure 16:
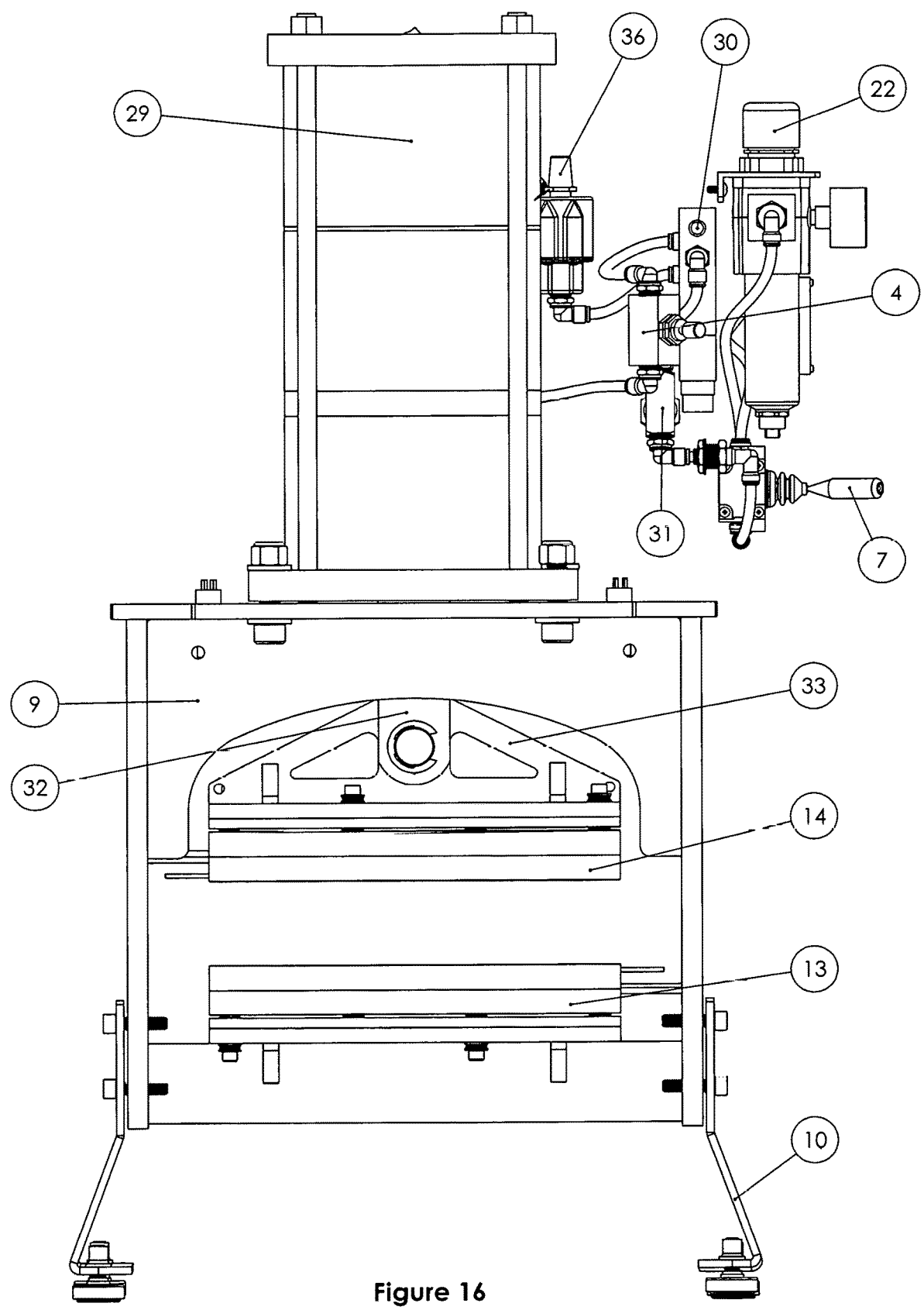
FIG. 16 is a front cutaway schematic view of a heated press.

Referring now to FIG. 16, there is shown a front cutaway schematic view of heated press A, showing pneumatic cylinder 29, to which is operatively connected manual/automatic pressure regulator 22, and quick exhaust valve 36. Supporting pneumatic cylinder assembly 29 is main frame 9, directly mounted thereto in the preferred embodiment. Alternatively, pneumatic cylinder 29 may be indirectly mounted to main frame 9 via another subframe or structural component, not shown, but known to those skilled in the art. Lower heat platen assembly 13 and upper heat platen assembly 14, clevis 32, and truss 33 are mounted above pneumatic cylinder assembly 29. Truss 33 is attached to upper heat platen 14 and provides both movement and alignment of heat platen assemblies 13, 14.

A 0.010" gap between the top surface of actuating truss 33 and clevis 32 allows for angular movement of the upper heat platen 14 relative to the lower heat platen 13. This ensures full contact between heat platens 13, 14 and the biological plant material being pressed, and reduces the angular stress on cylinder rod 39. The actuating force from cylinder rod 39 is transferred to actuating truss 33 via clevis pin 42, which pushes on the center bore of actuating truss 33. The triangular shape of actuating truss 33 transfers this force evenly across the entire length of heat platen 14. Supporting gussets, not shown, distribute this force over the width of heat platen 14.

Pneumatic multi-power cylinder 29, such as manufactured by the Fabco Company, operates at pressures between 0 and 150 psi, but in other embodiments could be operated at pressures up to 250 psi. Moreover, in alternate embodiments, pneumatic cylinder 29 could be replaced with a hydraulic piston system or a manual or electronic linear actuator, not shown.

Figure 17:
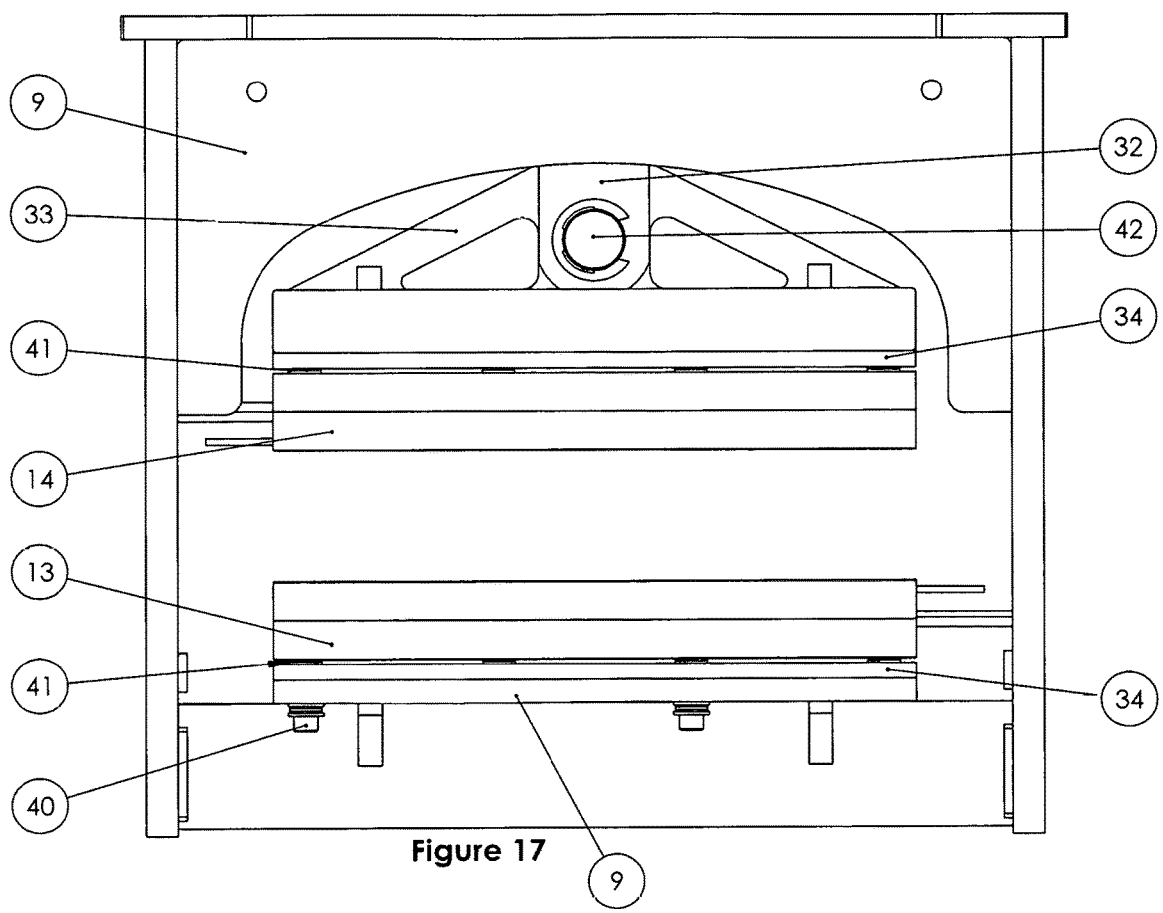
FIG. 17 is an enlarged cutaway schematic view of upper and lower heat platen assemblies in an open position.

Referring now to FIG. 17, there is shown an enlarged cutaway schematic view of lower and upper heat platen assemblies 13, 14 in an open, spaced-apart position. Clevis pin 42 is inserted into clevis 32, as shown. Insulating washers 43 are disposed below and above corresponding insulation layers 34 above upper heat platen assembly 14 and lower heat planet assembly 13, respectively, to isolate heat platens 13, 14 from insulation 34, creating an air gap to improve thermal isolation. Insulating washers 41 are sandwiched between steel washers 43 on the head of the screw to further improve thermal isolation. Insulation layers 34 are formed of high compression strength fiberglass insulation material with low thermal conductivity. Heat platen mounting screws 40 connect lower heat platen assembly 13 and insulation layer 34 to main frame 9.

Figure 18:
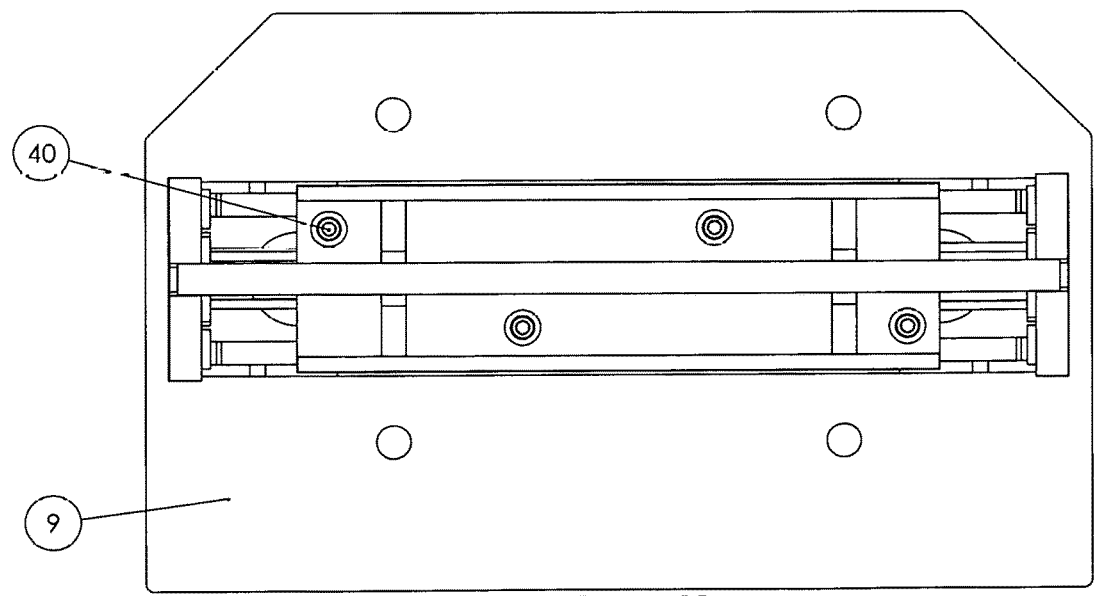
FIG. 18 is a bottom schematic view of the enlarged cutaway schematic view of upper and lower heat platen assemblies as shown in FIG. 17.

Referring now also to FIG. 18, there is shown a bottom schematic view of the enlarged cutaway schematic view of lower and upper heat platen assemblies 13, 14, as shown in FIG. 17.

Figure 19:
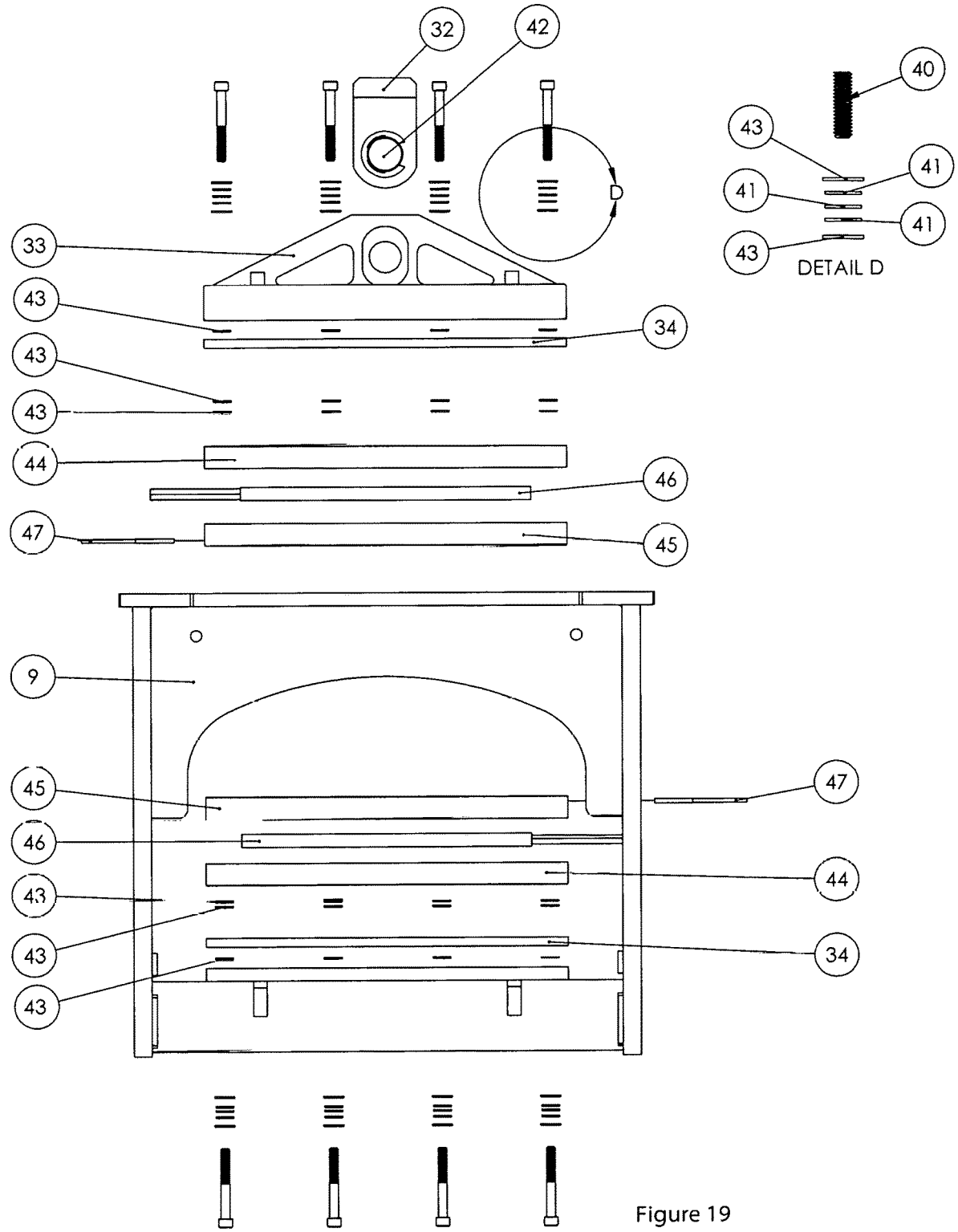
FIG. 19 is a an exploded schematic view of upper and lower heat platen assemblies, clevis, and insulation.

Referring now to FIG. 19, there is shown an exploded schematic view of back half 44 and front half 45 of lower and upper heat platen assemblies, 13, 14. The front half 45 of heat platen has a thermocouple 47 inserted therein. Clevis 32, clevis pin 42, and insulation layers 34 with associated insulating washers 43 are also shown in FIG. 19. Heat rods 46 are embedded in heat platen assemblies 13, 14. Heat platens 13, 14 are machined to clamshell around heat rods 46, but in other embodiments could be cast with heating elements enclosed. Heat rods 46 must have no more than 0.001" clearance relative to heat platens 13, 14 for property heat transfer. Likewise, thermocouple 47 is inserted into a machined hole in heat platens 13, 14 with less than 0.001" clearance for accurate temperature readings.

Figure 20:
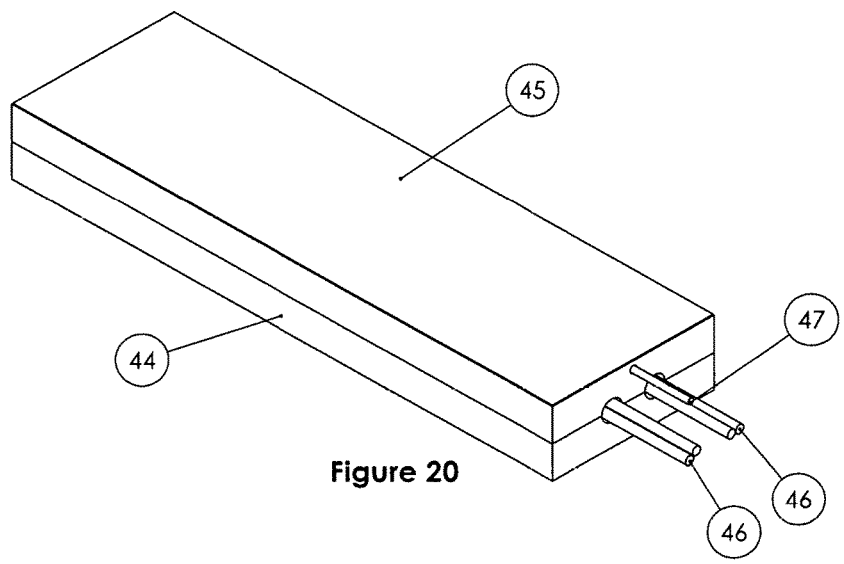
FIG. 20 is a schematic view of front and back halves of a heat platen with heat rods and thermocouple inserted therein.

Referring now to FIG. 20, there is shown a schematic view of back and front halves 44, 45 of a heat platen 13 or 14 with heat rods 46 and a respective isolated thermocouple 47 embedded therein.

Figure 21:
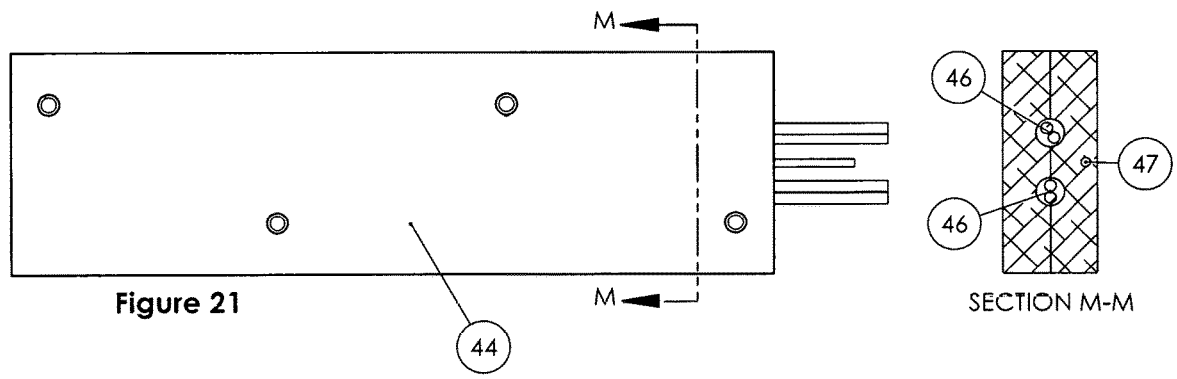
FIG. 21 is a bottom view of heat platen shown in FIG. 20.

Referring now to FIG. 21, there is shown a plan view of a heat platen 13 or 14, as shown in FIG. 20. Heat rods 46 and an isolated thermocouple 47 extend therefrom.

Figure 22:
FIG. 22 is a side view of heat platen shown in FIG. 20.

Referring now to FIG. 22, there is shown a side view of a heat platen 13 or 14, as shown in FIG. 20. Heat rods 46 and a thermocouple 47 extend therefrom.

Figure 23:
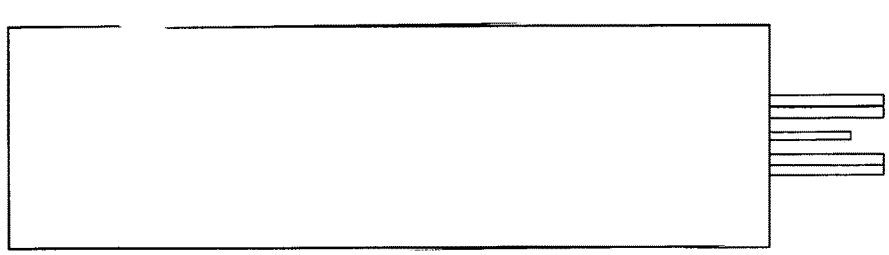
FIG. 23 is top view of heat platen shown in FIG. 20.

Referring now to FIG. 23, there is shown a bottom view of a heat platen 13 or 14, as shown in FIG. 20. Heat rods 46 and a thermocouple 47 extend therefrom.

Referring now to FIG. 24, there is shown a perspective view of a clevis 32 and actuating truss 33. Clevis pin 42 is inserted in clevis 32 and secured with a C-clip 48.

Referring now to FIG. 25, there is shown a plan view of clevis 32 and actuating truss 33, as shown in FIG. 24.

Referring now to FIG. 26, there is shown a front view of clevis 32 and actuating truss 33, as shown in FIG. 24.

Figure 27:
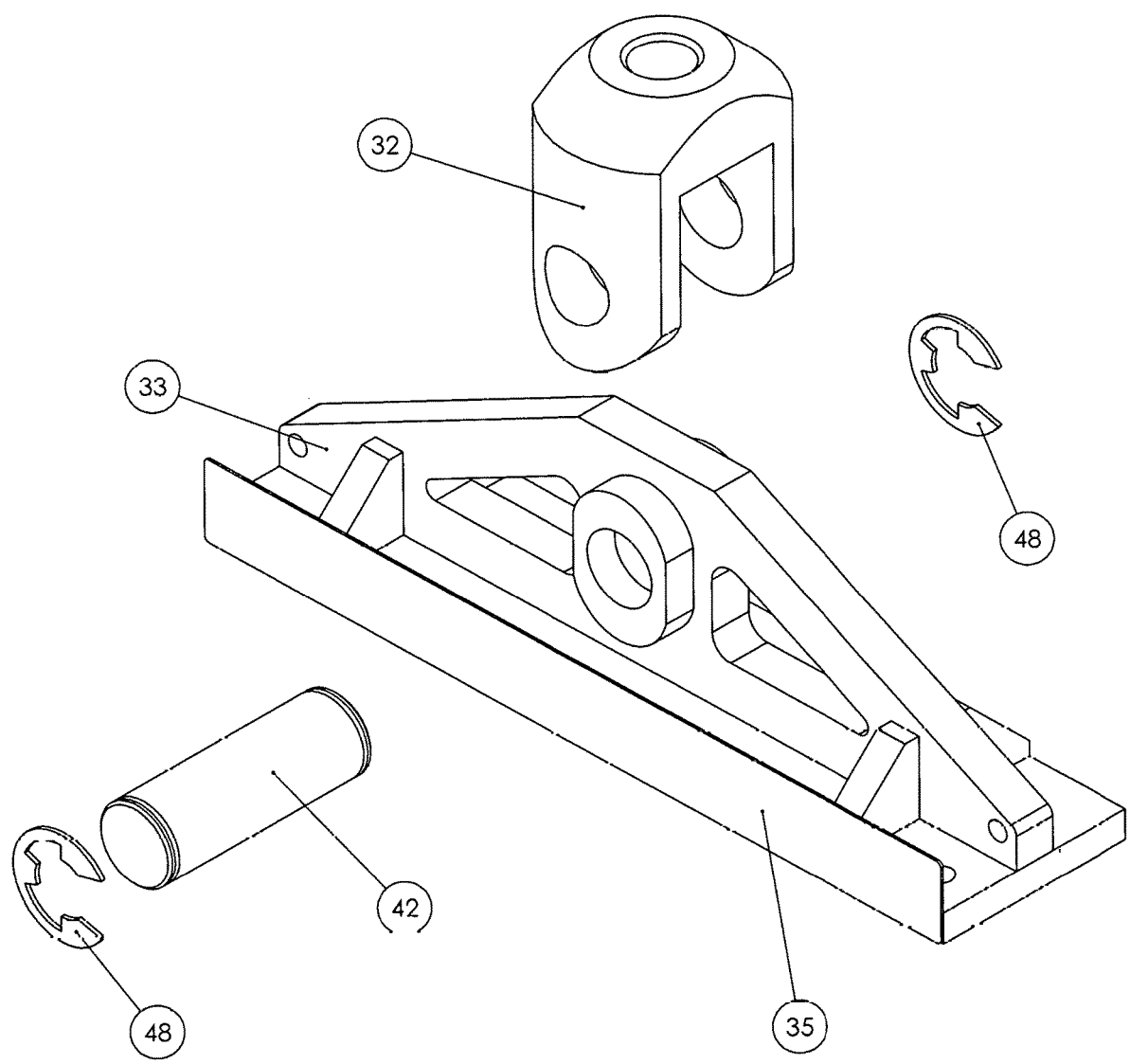
FIG. 27 is an exploded view of clevis, actuating truss, and clevis pin shown in FIG. 24.

Referring now to FIG. 27, there is shown an exploded, perspective view of clevis 32, actuating truss 33, and clevis pin 42 with C-clip 48, as shown in FIG. 24. A pinch guard 35 is attached along the base of clevis assembly 32, as shown.

Actuating truss 33 is mounted to pneumatic cylinder rod 39 via a standard rod clevis 32. In other embodiments pneumatic cylinder rod 39 could be replaced with a rotating rod and external guides, not shown, to prevent rotation of heat platen 13. Actuating truss 33 provides the structure to take a point load force from pneumatic cylinder 29 and distribute that force evenly over upper heat platen 14. Lower heat platen 13 is mounted in a similar fashion to main frame 9. Actuating truss 33 is machined to have a 0.010" gap between the top of truss 33 and clevis 32 to allow angular movement. This movement reduces stress on cylinder rod 39 and improves contact with the biological plant material being pressed.

Main frame 9 provides the structure to resist the force from pneumatic cylinder 29 and is designed to maintain rigidity and minimize deflection. Actuating truss 33 and main frame 9 work together to provide an even force distribution over the entire surface of heat platens 13, 14. In the preferred embodiment, actuating truss 33 is made from welded A36 steel and directly mounted to the cylinder rod 39. In other embodiments, however, actuating truss 33 could be made from any other metal alloy and could be cast, forged, machined, or welded.

In the preferred embodiment, actuating truss 33 is mounted to cylinder rod 39 with a standard clevis, but in other embodiments truss 33 could be welded, threaded, bolted, pinned, mounted with a universal joint/ball joint, or connected with any other non-fixed mechanical attachment. In other embodiments, actuating truss 33 need not be directly mounted to cylinder rod 39, but could instead have an indirect mechanical interface, such as mechanical linkages, pressure/hydraulic reservoirs, or other means of transferring the motion of cylinder rod 39 to actuating truss 33. In other embodiments, an actuating truss could be used on both heat plates 13, 14 to achieve proper pressure distribution. In other embodiments, actuating truss 33 could also be mounted with a universal or ball joint to allow angular movement in multiple directions. In the preferred embodiment, lower heat platen 13 is mounted to main frame 9 and fixed, although in other embodiments, lower heat platen 13 could have one or more degrees of freedom similar to actuating truss 33 to ensure proper contact with biological plant material being pressed.

Figure 28:
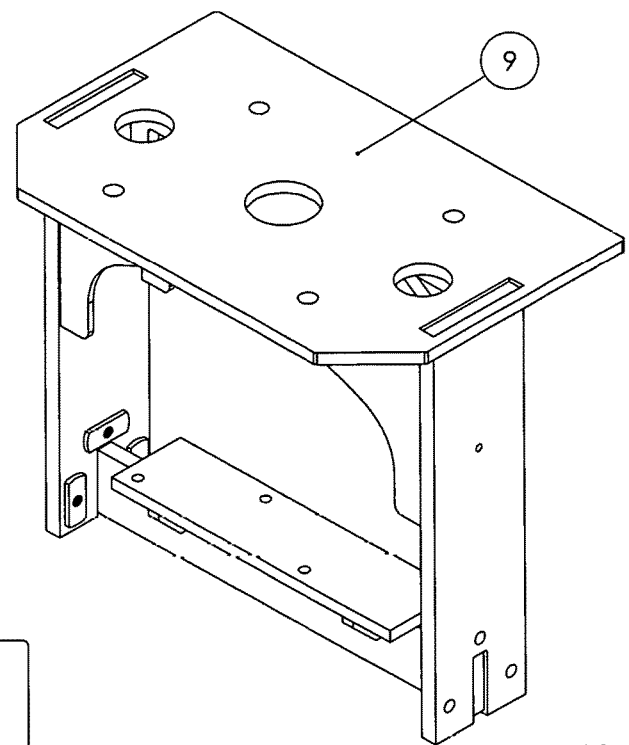
FIG. 28 is a perspective view of an unpopulated main frame of a heated press.

Referring now to FIG. 28, there is shown a perspective view of an unpopulated main frame 9 of heated press A. Main frame 9 is made from welded A36 steel in the preferred embodiment, or other metal or metal alloy that is cast, forged, machined, or welded, and is capable of ensuring rigidity under load and forces from pneumatic cylinder 29.

Figure 29:
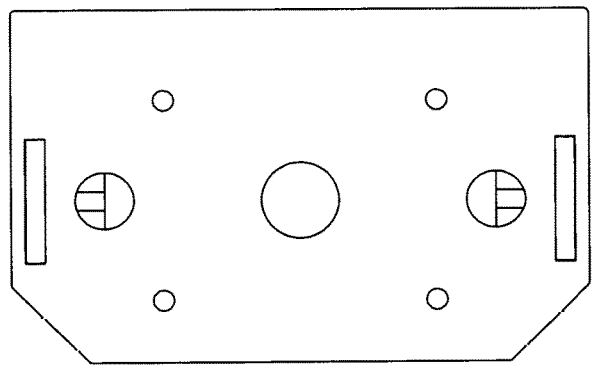
FIG. 29 is a top view of the unpopulated main frame of the heated press shown in FIG. 28.

Referring now to FIG. 29, there is shown a top view of the main frame 9 of heated press A, as shown in FIG. 28.

Figure 30:
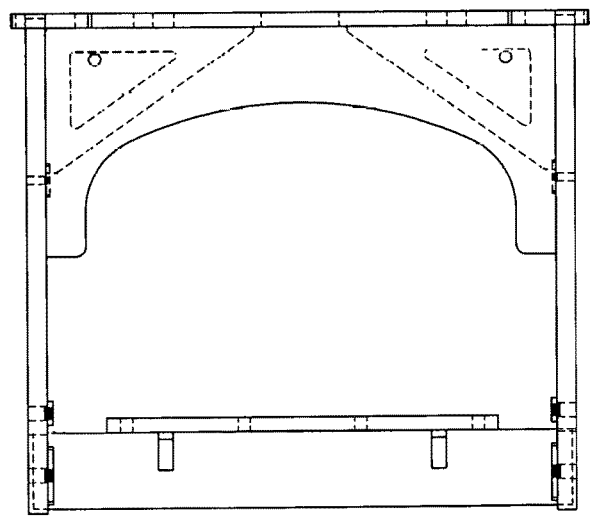
FIG. 30 is a plan view of the unpopulated main frame of the heated press shown in FIG. 28.

Referring now to FIG. 30, there is shown a plan view of the main frame 9 of heated press A, as shown in FIG. 28.

Figure 31:
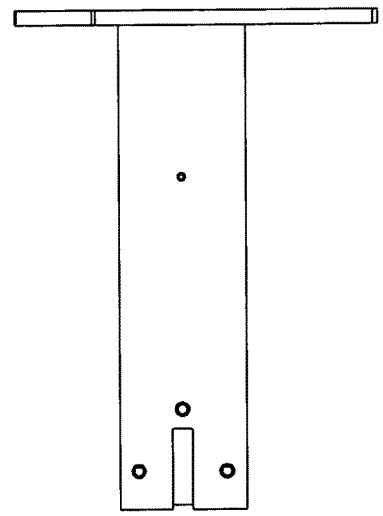
FIG. 31 is a right schematic view of the unpopulated main frame of the heated press shown in FIG. 28.

Referring now to FIG. 31, there is shown is a right schematic view of the main frame 9 of heated press A, as shown in FIG. 28.

Figure 32:
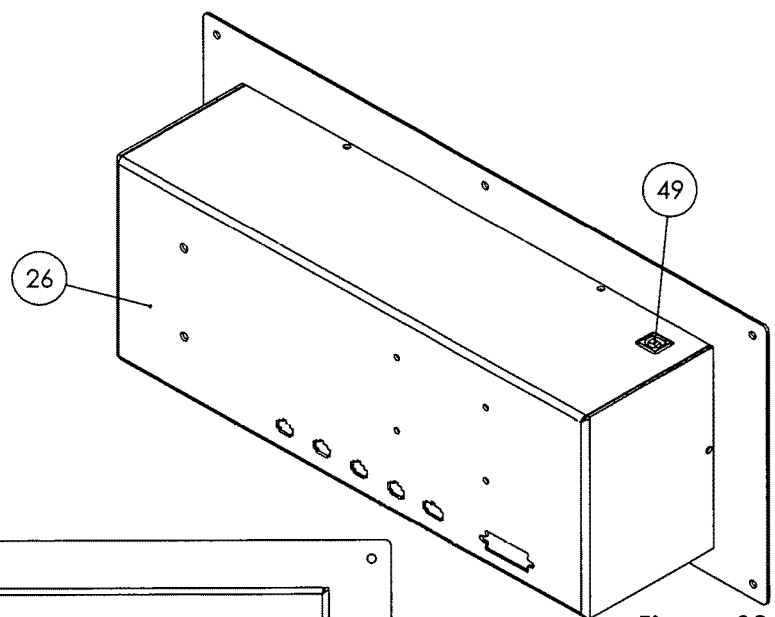
FIG. 32 is a perspective view of an electrical enclosure for use with a heated press.

Referring now to FIG. 32, there is shown a perspective view of electrical enclosure 26 and USB firmware port 49 for use with heated press A. USB firmware port 49 allows the operator to update firmware easily. Quick electrical connections 50 allow the operator to remove and/or replace the entire electrical enclosure 26, which mounts to main enclosure 17 as a modular unit.

Figure 33:
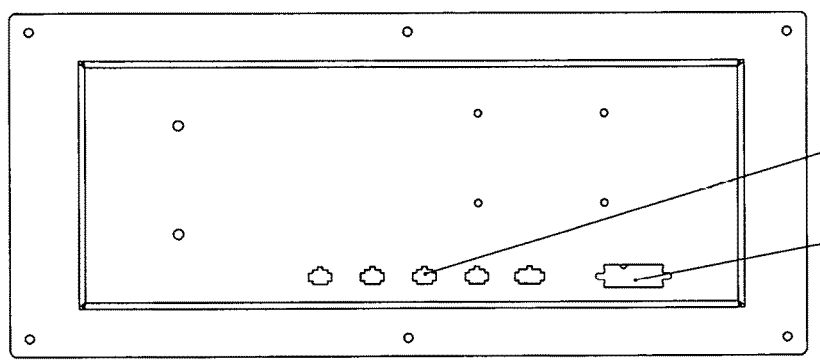
FIG. 33 is a rear view of the electrical enclosure for use with a heated press shown in FIG. 32.

Referring now to FIG. 33, there is shown a front view of electrical enclosure 26, as shown in FIG. 32. Quick electrical connections are shown as reference numerals 50.

Figure 34:
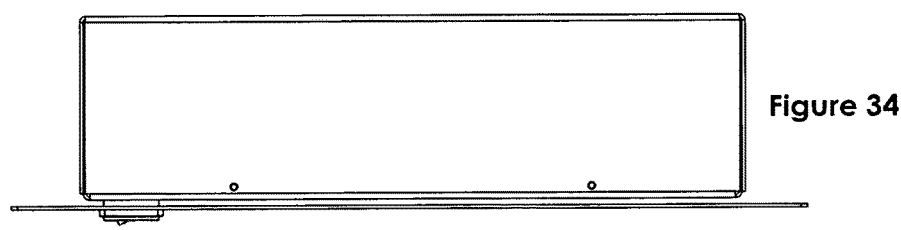
FIG. 34 is a top view of the electrical enclosure for use with a heated press shown in FIG. 32.

Referring now to FIG. 34, there is shown a plan view of electrical enclosure 26, as shown in FIG. 32.

Figure 35:
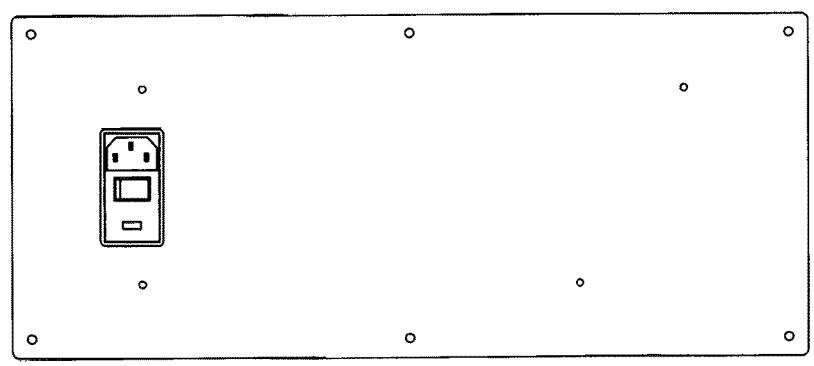
FIG. 35 is a front view of the electrical enclosure for use with a heated press shown in FIG. 32, showing a power entry module.

Referring now to FIG. 35, there is shown a rear view of electrical enclosure 26 and power entry module 25, as shown in FIG. 32.

Figure 36:
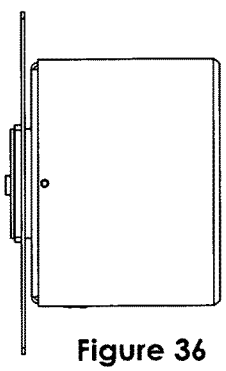
FIG. 36 is a side view of the electrical enclosure for use with a heated press shown in FIG. 32.

Referring now to FIG. 36, there is shown a side view of electrical enclosure 26 and power entry module 25, as shown in FIG. 32.

Figure 37:
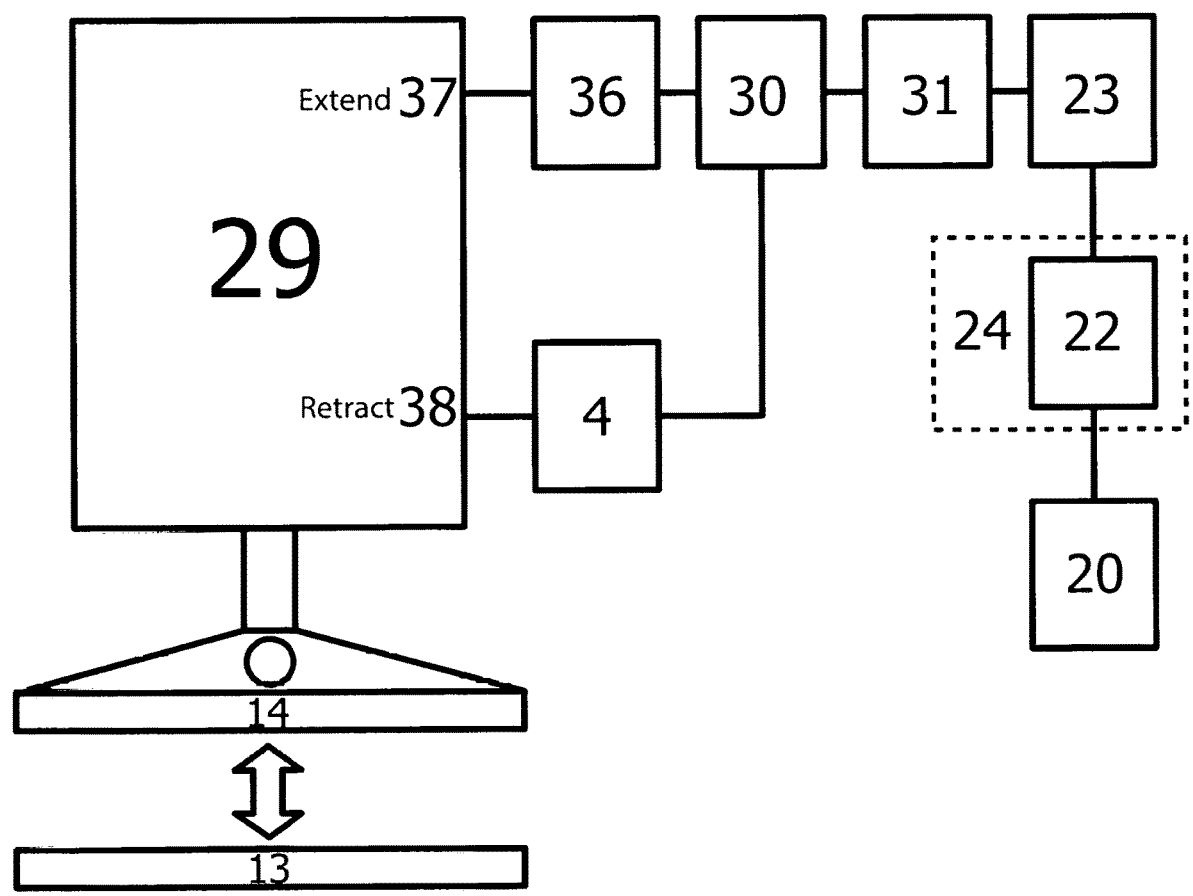
FIG. 37 is a block diagram of the major components of a heated press having a single pressure regulator system.

Referring now to FIG. 37, there is shown a block diagram of the major components of a heated press A having a single manual/automatic pressure regulator system 22. Pneumatic cylinder 29, mounted above lower and upper heat platen assemblies 13, 14, has cylinder inlet (extend) 37 and cylinder inlet (retract) 38, to which are operatively connected quick exhaust valve 36 and actuation speed controller 4, respectively. Operatively connected to quick exhaust valve 36 is a directional solenoid valve 30, also connected to actuation speed controller 4, directional solenoid valve 30 being connected to a pressure transducer 31 and, thence, to pneumatic bulkhead 23. Directional solenoid valve 30 determines whether pneumatic cylinder 29 is retracted or extended. As air flows to extend cylinder 29, it passes through quick exhaust valve 36 and into cylinder inlet 37. Air within cylinder 29 on the opposite side of the piston must be exhausted in order for actuation to occur. That air is throttled by directional solenoid valve 30 under control of actuation speed controller 4 which, in turn, controls the speed of movement of heat platen 14 as it actuates. Thus, directional solenoid valve 30 switches to supply air to cylinder inlet (retract) 38 through speed controller 4. Upon retracting heat platen 14, the air within cylinder 29 is exhausted via quick exhaust valve 36, which allows for a rapid response.

Pressure transducer 31 sends a signal to electronic controls to report actual air pressure. Connected to pneumatic bulkhead 23 is the aforementioned manual/automatic pressure regulator system 22 and associated single pressure regulator system 24. Inlet air quick connect 20 is connected to pressure regulator system 22 or 24. Compressed air enters main enclosure 17 via pneumatic bulkhead 23.

Figure 38:
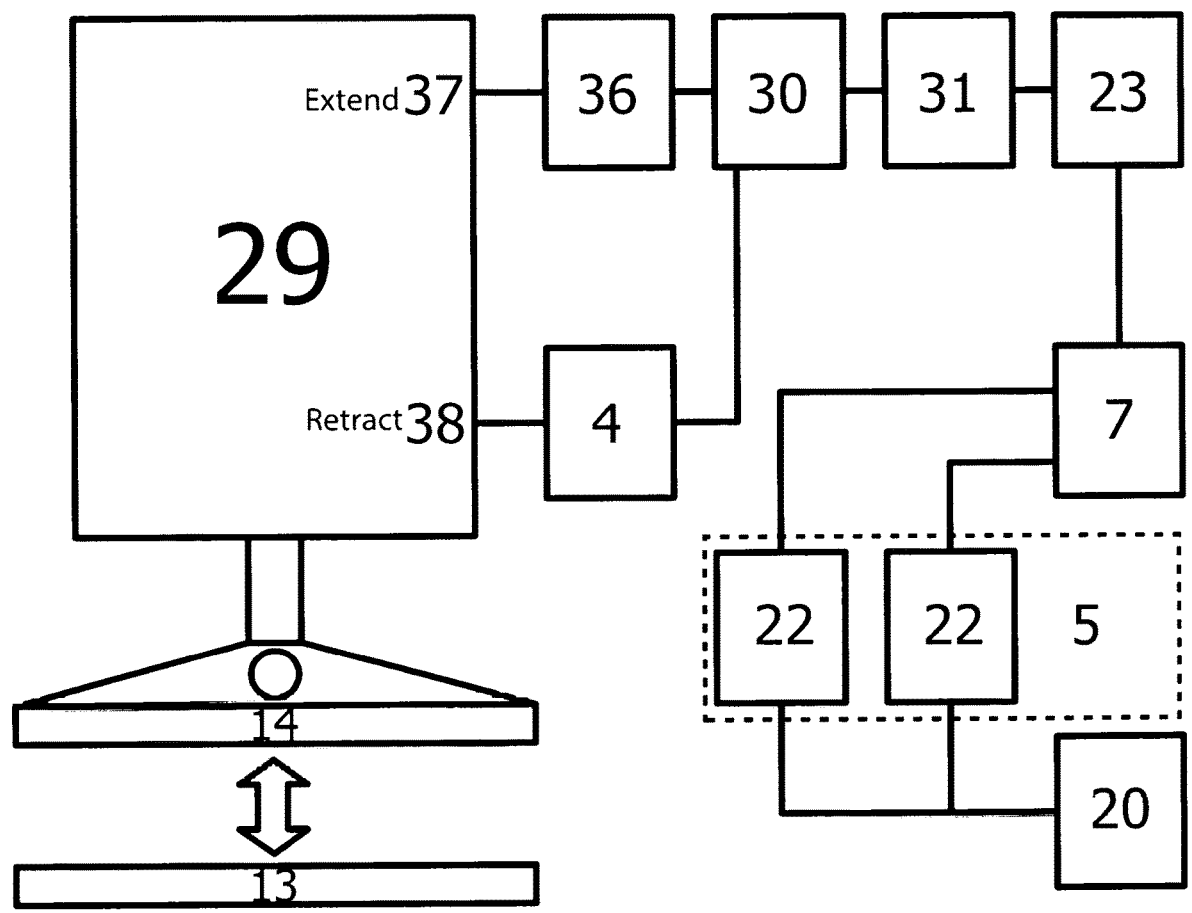
FIG. 38 is a block diagram of the major components of a heated press having a dual pressure regulator system.

Referring now to FIG. 38, there is shown a block diagram of the major components of a heated press having a dual pressure regulator system 5. Pneumatic cylinder 29, mounted above lower and upper heat platen assemblies 13, 14, has cylinder inlet (extend) 37 and cylinder inlet (retract) 38, to which are operatively connected quick exhaust valve 36 and actuation speed controller 4, respectively. Operatively connected to quick exhaust valve 36 is directional solenoid valve 30, also connected to actuation speed controller 43, directional solenoid valve being connected to pressure transducer 31 and, thence, to pneumatic bulkhead 23. Connected to pneumatic bulkhead 23 is pressure controller lever 7, which operates one or both manual/automatic pressure regulators 22 or dual pressure regulator system 5. Inlet air quick connect 20 is connected to one or both manual/automatic pressure regulators 22.

Figure 39:
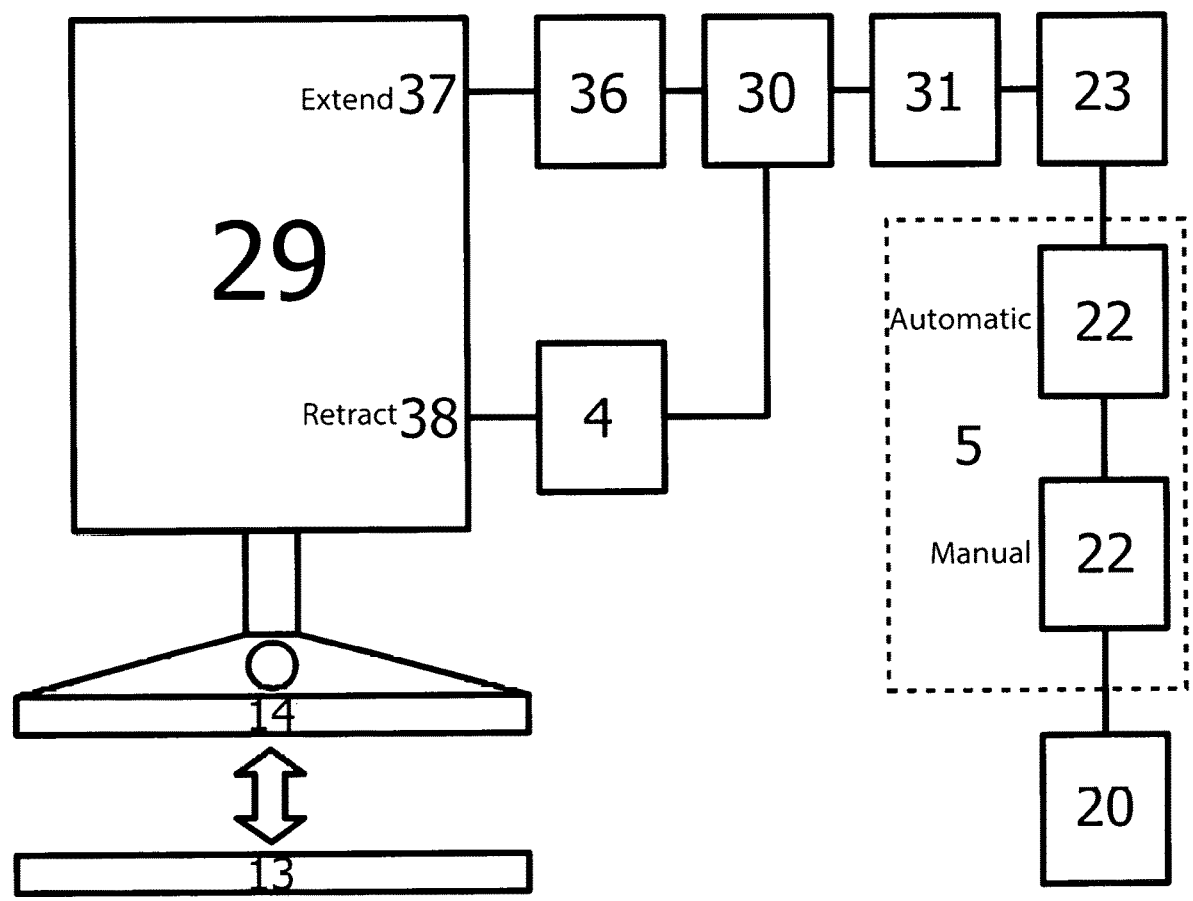
FIG. 39 is a block diagram of the major components of a heated press having a manual and automatic pressure regulator system.

Referring now to FIG. 39, there is shown a block diagram of the major components of a heated press A having a dual pressure regulating system 5 that consists of a manual pressure regulating and also an automatic pressure regulator system 22 that works in conjunction therewith. Pneumatic cylinder 29, mounted above lower and upper heat platen assemblies 13, 14, has cylinder inlet (extend) 37 and cylinder inlet (retract) 38, to which are operatively connected quick exhaust valve 36 and actuation speed controller 4, respectively. Operatively connected to quick exhaust valve 36 is a directional solenoid valve 30, to which is also connected actuation speed controller 4 and to a pressure transducer 31 and, thence, to pneumatic bulkhead 23. Connected to pneumatic bulkhead 23 is dual pressure regulator system 5 consisting of manual/automatic pressure regulators 22. Inlet air quick connect 20 is connected to dual pressure regulator system 5.

In operation, a folded sheet of parchment paper is placed on lower heat platen 13 and a biological plant or portion thereof is placed between the folded sheets of parchment paper. The biological plant is placed within the folded sheet of parchment paper and secured by parchment paper retaining clips 11. Parchment paper clips 11 position the parchment paper at an angle such that the biological plant material being pressed is automatically centered on the lower heat platen 13. Parchment paper clips 11 are mounted to the platen cover 18, which protects the user from pinch points and burns. Main enclosure 17 houses most of the internal workings of heat press A.

The plant material is usually but not always placed inside a filtration bag, not shown. When it is pressed, the oils are liquefied and forced out of the filtration bag or away from the plant material where they collect and cool on the parchment paper. Alternatively, the press may be used in the horizontal orientation, in which case the oils may flow down via gravity and drip onto a collection sheet or container. The oils may then be scraped and collected from either the parchment paper or the collection chamber.

Compressed air powers pneumatic cylinder 29 via actuation speed controller 4 to move upper heat platen 14 downwardly towards lower heat platen 13. Air pressure is regulated using dual pressure regulator system 5, 7 in this embodiment. In alternative embodiments, a single pressure regulator system 24 can be used in place of dual regulator system 5, 7. Either a manual or automatic pressure regulator 22 can be used to control the pressing force.

The speed at which the upper heat platen 14 moves downwardly is controlled by actuation speed controller 4. Movement of upper heat platen 14 is initiated when the operator presses the two start buttons 8 and can be cancelled when he presses the stop button on the touchscreen or the emergency stop button 16. The operator can control the temperature of the platens 13, 14 up to 300° F. The operator can also control time to press, pressure developed between heat platens 13, 14, and many other functions through use of user keypad 3 and LCD display 2, mounted to user interface panel 1. In other embodiments, user keypad 3 and LCD display 2 could be replaced with any human machine interface (HMI), including touch screens or keypad devices.

The first position of pressure control lever 7 utilizes the air supplied by pressure regulator 22 on the left, the second position is OFF, and the third position utilizes the air supplied by pressure regulator 22 on the right. This allows the operator to quickly switch between two preset pressures to change the pressing force between the heat platens. This also allows the operator to slowly ramp up pressure from the lower pressure to the higher pressure over time. The operator may start in position 1 and then move into position 2 which is off. As the operator makes quick movements from position 2 to position 3 and back to position 2, the high air pressure is slowly bled into the pneumatic cylinder 29, increasing the pressing force. The operator may perform this repeatedly, slowly increasing the pressure until he decides to go to position 3 and leave it there. Dual pressure regulator system 5 allows full control of air pressure between the two boundary pressure limits set by each pressure regulator 22.

There are a few key variables when extracting oils using a heated press. These primary variables include the temperature of each heat plate and the pressing force/time associated with each pressing force, which changes over time. The secondary variables include, but are not limited to, the type of material being pressed, the quality and consistency of the material, the size (length×width) and mesh rating (microns) of the filter material, the weight of the material, the relative humidity content of the material, as well as the orientation of the press. The control system of the present invention can manage each one of these variables to ensure the highest yield and quality of oil while minimizing material loss.

When pressing plant material for oil extraction, the most common failure is a filter blowout, which causes oil contamination and a material loss, financially affecting the user detrimentally. Similarly, the filter material may remain intact, but too much force is used, and undesirable material will be forced through the filtration material and degrade the potency and quality of the oil. On the other side of the spectrum, under-pressing a material with insufficient force can result in a low yield and, again, will financially affect the user detrimentally. The highest quality oil is extracted with just enough pressure to escape the filter material but not too much to include undesirables.

The pressing time and temperatures are also important to properly preserve the quality and consistency of the oil. Pressing too hot or letting the oil cook on the heat plates can evaporate terpenes (i.e., natural oils in plant material that contribute to flavor, smell, and texture). The controls of the present invention monitor all these variables to minimize bag blowouts and undesirables, increase yields, and improve quality and consistency of the extracted oils.

Figure 40:
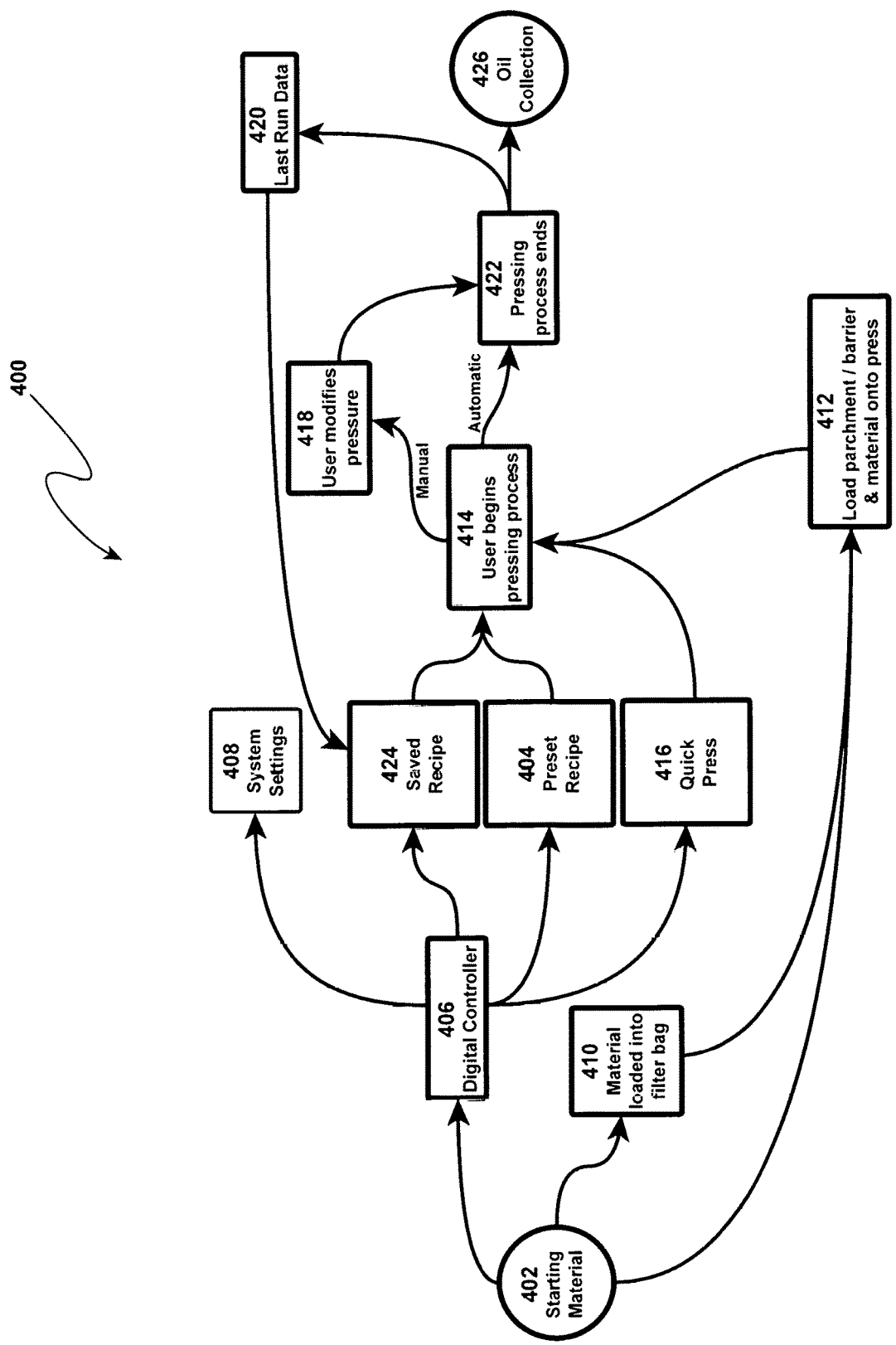
FIG. 40 is a flow chart of system operations.

Referring now to FIG. 40, there is shown a flow chart 400 of system operations. The user, not shown, has three options when choosing how to operate press A. First, the user provides the control system with information regarding what type of material is to be pressed 402, as well as the quantity of that material. A suggested preset recipe 404 is created by digital controller, step 406, operatively connected to system settings 408. The user loads the material in a filter bag, step 410, loads parchment paper in press A 412, and begins the press cycle 414.

With a manual system, on-screen prompts direct the user when and how to adjust the variables to match the recipe 404. Temperatures are monitored electronically. With a digital system, the controls change these variables automatically according to the specifics of the recipe. At any point during the press cycle, the user can override any portion of the recipe and make on-the-fly changes. This is important because it allows the user to make a critical change that might prevent a failed result or scrapped material. The user is also able to make changes to the recipe afterwards and save any changes as a new recipe.

The second option for the user is to create a recipe from scratch using the Quick Press feature 416. The user tells the control system 406 which temperatures to use for each heat plate, as well as a starting pressure/force prior to beginning the press cycle 414. The user may change the pressure 418 or temperature over time. Those results are recorded automatically as last run data 420. After a press cycle is complete 422, the user may review the recorded data 420, make changes, and record this data in a saved recipe 424 to be used later.

The third option the user has is to run a saved recipe 424. The user can store recipes 424 in the control system by creating a recipe using Quick Press 416, by modifying a preset recipe 404, or by manually entering the recipe data directly. At any point during operation, the user may view and edit these recipes before running them or the user can run a recipe and make changes on-the-fly.

As with any of these three pressing options 404, 416, and 424, the real-time press cycle data is always recorded as last run data 420 so the user can save a new recipe and make any necessary changes. Each recipe can store specific information regarding the secondary variables for that recipe including, but not limited to, material type, bag size, bag mesh rating, the weight of the material, the relative humidity content of the material, the orientation of the press, and a name for the recipe. This information allows an operator to run the machine unassisted, having every detail stored in a convenient and central location. Oil collection 426 proceeds normally as the pressing process continues.

The control system may also be connected to the Internet or other electronic devices using a wired or wireless connection. Networking the press allows the user to control the machine remotely, upload and download recipes that are created externally or internally, share recipes with other users or software programs, automatically update software, and record and transmit diagnostic and usage information. Other equipment, such as multiples presses, not shown, can also be synchronized and coordinated to aid the process.

Since other modifications and changes varied to fit particular operating requirements and environments will be apparent to those skilled in the art, the invention is not considered limited to the example chosen for purposes of disclosure and covers all changes and modifications which do not constitute departures from the true spirit and scope of this invention.

Having thus described the invention, what is desired to be protected by Letters Patent is presented in the subsequently appended claims.

What is claimed is:

1. A heat press for extracting oil from a biological plant, comprising:
   a) a main frame;
   b) a first heat platen fixedly attached to said main frame;
   c) a retractable second heat platen positioned opposite said first heat platen;
   d) actuation means operatively connected to said second heat platen for initiating movement thereto, said actuation means comprising a truss operatively connected to a clevis;
   e) means for providing force to said actuation means;
   f) control means comprising a regulator system chosen from a group of: a single pressure regulator system, a dual pressure regulator system, and a digital regulator system, said regulator system being operatively connected to said actuation means for controlling pressure of a pressing operation of said heat press;

g) a user interface panel comprising at least one component selected from the group: LCD display, touchscreen, and user keyboard; and h) whereby said heat press is operational in an orientation selected from the group: vertical, horizontal, and a position intermediate vertical and horizontal.

2. The heat press for extracting fluid from a biological plant in accordance with claim 1, wherein said means for providing force to said actuation means comprises at least one mechanism chosen from a group: pneumatic cylinder, hydraulic cylinder, and linear actuator.

3. The heat press for extracting fluid from a biological plant in accordance with claim 1, wherein at least one of said second and first heat platens comprises heating elements and an isolated thermocouple.

4. The heat press for extracting fluid from a biological plant in accordance with claim 1, further comprising a power entry module for accepting a source of electrical power.

5. The heat press for extracting fluid from a biological plant in accordance with claim 1, further comprising parchment paper for sandwiching said biological plant therebetween.

6. The heat press for extracting fluid from a biological plant in accordance with claim 1, further comprising a layer of insulation comprising high compression strength fiberglass insulation material with low thermal conductivity proximate at least one of said second and first heat platens.

7. A heat press for extracting oil from a biological plant, comprising:
   a) a main frame;
   b) a removable first heat platen attached to said main frame;
   c) a removable retractable second heat platen positioned opposite said first heat platen;
   d) actuation means operatively connected to said second heat platen for initiating movement thereto, said actuation means comprising a truss operatively connected to a clevis; and
   e) means for providing force to said actuation means.

8. The heat press for extracting oil from a biological plant in accordance with claim 7, wherein said means for providing force to said actuation means comprises at least one mechanism chosen from a group: pneumatic cylinder, hydraulic cylinder, and linear actuator.

9. The heat press for extracting fluid from a biological plant in accordance with claim 7, further comprising a user interface panel comprising at least one component selected from the group: LCD display, touchscreen, and user keyboard.

10. The heat press for extracting fluid from a biological plant in accordance with claim 7, further comprising a power entry module for accepting a source of electrical power.

11. The heat press for extracting fluid from a biological plant in accordance with claim 7, further comprising parchment paper for sandwiching said biological plant therebetween.

12. The heat press for extracting fluid from a biological plant in accordance with claim 11, further comprising parchment paper retaining clips for positioning said parchment paper relative to said second and first heat platens.

13. The heat press for extracting fluid from a biological plant in accordance with claim 7, further comprising a layer of insulation proximate at least one of said second and first heat platens.

14. A heat press for extracting fluid from a biological plant, comprising:
   a) a main frame;
   b) a first heat platen attached to said main frame;
   c) a retractable second heat platen positioned opposite said first heat platen;
   d) actuation means operatively connected to said second heat platen, said actuation means comprising a truss operatively connected to a clevis;
   e) means for providing force to said actuation means; and
   f) control means operatively connected to said actuation means for controlling pressure, time, and temperature of a pressing operation of said heat press.

15. The heat press for extracting fluid from a biological plant in accordance with claim 14, wherein said means for providing force to said actuation means comprises at least one mechanism chosen from a group: pneumatic cylinder, hydraulic cylinder, and linear actuator.

16. The heat press for extracting fluid from a biological plant in accordance with claim 14, wherein at least one of said second and first heat platens comprises at least one heating element.

17. The heat press for extracting fluid from a biological plant in accordance with claim 14, wherein said control means comprises a regulator system chosen from a group of: a single pressure regulator system, a dual pressure regulator system, and a digital regulator system.

18. The heat press for extracting fluid from a biological plant in accordance with claim 14, further comprising a user interface panel comprising at least one component selected from the group: LCD display, touchscreen, and user keyboard.

19. The heat press for extracting fluid from a biological plant in accordance with claim 14, further comprising parchment paper for sandwiching said biological plant therebetween and parchment paper retaining clips for positioning said parchment paper relative to said second and first heat platens.

20. The heat press for extracting fluid from a biological plant in accordance with claim 14, further comprising a layer of insulation proximate at least one of said second and first heat platens.

21. A heat press for extracting oil from a biological plant, comprising:
   a) a main frame;
   b) a first heat platen attached to said main frame;
   c) a retractable second heat platen positioned opposite said first heat platen;
   d) actuation means operatively connected to said second heat platen for initiating movement thereto, said actuation means comprising a truss operatively connected to a clevis; and
   e) control means comprising a pressure regulator chosen from a group consisting of: a single pressure regulator system and a dual pressure regulator system, either pressure regulator system being operable by a method chosen from a group consisting of: manually and electronically, said control means being operatively connected to said actuation means for controlling time and temperature of a pressing operation of said heat press.

22. The heat press for extracting fluid from a biological plant in accordance with claim 21, further comprising a layer of insulation proximate at least one of said second and first heat platens.

* * * * *